US008206725B2

(12) United States Patent
Good et al.

(10) Patent No.: US 8,206,725 B2
(45) Date of Patent: Jun. 26, 2012

(54) IMMUNOGENIC AGENT AND PHARMACEUTICAL COMPOSITION FOR USE AGAINST HOMOLOGOUS AND HETEROLOGOUS PATHOGENS INCLUDING PLASMODIUM SPP

(75) Inventors: Michael Good, The Gap (AU); Mary M Stevenson, Montreal (CA)

(73) Assignees: The Council of the Queensland Institute of Medical Research, Herston (AU); McGill University, Montreal (CA)

( * ) Notice: Subject to any disclaimer, the term of this patent is extended or adjusted under 35 U.S.C. 154(b) by 0 days.

(21) Appl. No.: 10/569,703

(22) PCT Filed: Jun. 30, 2004

(86) PCT No.: PCT/AU2004/000870
§ 371 (c)(1),
(2), (4) Date: Sep. 1, 2006

(87) PCT Pub. No.: WO2005/018665
PCT Pub. Date: Mar. 3, 2005

(65) Prior Publication Data
US 2007/0110771 A1    May 17, 2007

(30) Foreign Application Priority Data

Aug. 26, 2003   (AU) ............................... 2003904598

(51) Int. Cl.
*A61K 39/015*   (2006.01)
*A61K 39/00*    (2006.01)
*A01N 63/00*    (2006.01)
*A01N 65/00*    (2009.01)

(52) U.S. Cl. ................. 424/272.1; 424/93.1; 424/184.1; 424/265.1; 424/268.1; 424/269.1

(58) Field of Classification Search ........................ None
See application file for complete search history.

(56) References Cited

U.S. PATENT DOCUMENTS

| 5,547,852 A * | 8/1996 | Seiler et al. ..................... 435/29 |
| 5,571,515 A * | 11/1996 | Scott et al. ..................... 424/208.1 |
| 5,650,492 A * | 7/1997 | Gately et al. ..................... 530/351 |
| 2003/0091599 A1 * | 5/2003 | Davis et al. ..................... 424/278.1 |

OTHER PUBLICATIONS

Stevenson et al. Journal of Interferon and Cytokine Research vol. 22, supplement 1, p. s-184, Sep. 2002.*
Pombo et al. Lancet 2002; 360:610-17.*
Sakai et al. Parasitology International (1999) 4827-33.*
Kenney et al. The Journal of Immunology, 1999, 163:4481-4488.*
Abbas et al. Cellular and Molecular Immunology 4$^{th}$ edition 2000 p. 483.*
Jennings et al. Infection and Immunity , Dec. 1998 p. 5972-5979.*
Aste-Amezaga et al. The Journal of Immunology, 1998, 160:5936-5944.*
Hirunpetcharat et al. Vaccine. Jun. 20, 2003 pp. 2923-2932.*
Trinchieri et al. Immunological Research 1998; 17/1 &2:269-278.*
Playfair et al (Immunology 1977 33:507-515).*
Lyold L. Smrkovski. Phil J Microbiol Infect Dis. 1981; 10(1):7-12.*
Siddiqui et al. Science. Mar. 1977, 197:388-389.*
Mendis et al. Parasite Immunology 1982, 4, 117-127.*
McColm et al. (Annals of Tropical Medicine and Parasitology (Aug. 1983): 77(4) 355-377).*
Hommel et al (Ann. Immunol. (Inst. Pasteur) 1982, 133C, 57-67).*
Pinzon-Charry et al. The Journal of Clinical Investigation, vol. 20, issue 8, p. 2967-2978, 2010.*
Hirunpetcharat, C., et al., CpG Oligodeoxynucleotide Enhances Immunity Against Blood-Stage Malaria Infection in Mice Parenterally Immunized with a Yeast-Expressed 19 kDa Carboxyl-Terminal Fragment of Plasmodium Yoelii Merozoite Surface Protein-1 ($MSP1_{19}$) Formulated in Oil-Based Montanides, Vaccine, Feb. 2003, pp. 2923-2032, vol. 21.
Kumar, S., et al., CpG Oligodeoxynucleotide and Montanide ISA 51 Adjuvant Combination Enhanced the Protective Efficacy of a Subunit Malaria Vaccine, Infection and Immunity, Feb. 2004, pp. 949-957, vol. 72, No. 2.
Near, K., et al., Improved Immunogenicity and Efficacy of the Recombinant 19-Kilodalton Merozoite Surface Protein 1 by the Addition of Oligodeoxynucleotide and Alumninum Hydroxide Gel in a Murine Malaria Vaccine Model, Infection and Immunity, Feb. 2002, pp. 692-701, vol. 70, No. 2.
Sakai, T., et al., DNA Immunization with Plasmodium Falciparum Serine Repeat Antigen: Regulation of Humoral Immune Response by Coinoculation of Cytokine Expression Plasmid, Parasitology International (1999) pp. 27-33.
Sakai, T., et al., Gene Gun-Based Co-Immunization of Merozoite Surface Protein-1 cDNA with IL-12 Expression Plasmid Confers Protection Against Lethal Plasmodium Yoelii in A.J Mice, Vaccine 21 (2003), pp. 1432-1444.

(Continued)

Primary Examiner — Oluwatosin Ogunbiyi
(74) Attorney, Agent, or Firm — Leydig, Voit & Mayer, Ltd.

(57) ABSTRACT

The present invention relates to an immunogenic agent comprising a low dose of an antigenic component from one or more pathogens and an agent capable of increasing an amount of IL-12 in animal, and use thereof for reducing infection or improving recovery from an infection from the pathogen. The immunogenic agent preferably comprises CpG nucleic acid, IL-12 protein and/or IL-12 nucleic acid. The pathogen is preferably an intracellular pathogen comprising one or more species and strains, such as *Plasmodium* spp. The invention also relates to a pharmaceutical composition comprising the immunogenic agent. The pharmaceutical composition is preferably an immunotherapeutic composition. The immunotherapeutic composition, is preferably a vaccine capable of providing protection against or treating *Plasmodium* spp infection, the causative agent of malaria in humans.

27 Claims, 11 Drawing Sheets

OTHER PUBLICATIONS

Figure 1:
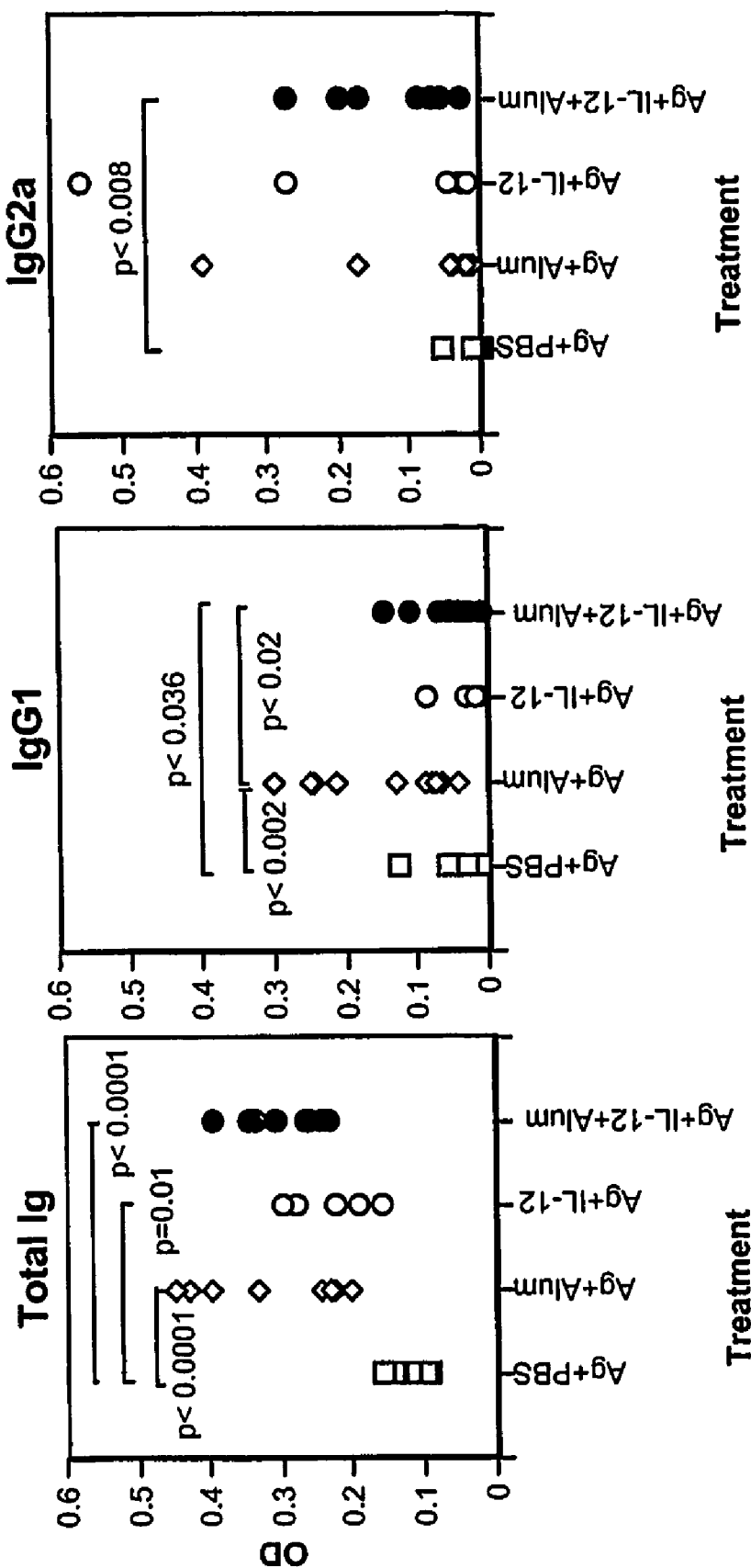

Soares, I., et al., Immunogenic Properties of the Plasmodium Vivax Vaccine Candidate $MSP1_{19}$ Expressed as a Secreted Non-Glycosylated Polypeptide from Pichia Pastoris, Parasitolog (2002), 124, 237-246.

Stevenson, M., et al., Modulation of Host Responses to Blood-Stage Malaria by Interleukin-12: from Therapy to Adjuvant Activity, Microbes and Infection 3, 2001, pp. 49-59.

Stevenson, M., et al., CPG DNA Enhances Immune Protection and Vaccination Efficacy Against Blood-Stage Plasmodium Chabaudi as Malaria Infection, Abstract, P-18-14, p. S-184.

Su, Z., et al., Vaccination with Novel Immunostimulatory Adjuvants Against Blood-Stage Malaria in Mice, Infection and Immunity, Sep. 2003, pp. 5178-5187, vol. 71, No. 9.

Yoshida, S., et al., Direct Immunization of Malaria DNA Vaccine into the Liver by Gene Gun Protects Against Lethal Challenge of Plasmodium Berghei Sporozoite, Biochemical and Biophysical Research Communications (2000), pp. 107-115, vol. 271, No. 1.

Good, M., "The Continuing Challenges of Malaria Vaccine Development," at *World Health Organization Global Vaccine Research Forum*, Jun. 30-Jul. 2, 2003, Seoul, Republic of Korea.

Good, M., "Will blood-stage malaria vaccines be developed using current strategies?," *Proceedings of the fourth Global Vaccine Research Forum*, Apr. 2004, pp. 1-2, section 1.1, WHO/IVB/04.09, World Health Organization, Geneva, Switzerland.

* cited by examiner

IMMUNOGENIC AGENT AND PHARMACEUTICAL COMPOSITION FOR USE AGAINST HOMOLOGOUS AND HETEROLOGOUS PATHOGENS INCLUDING PLASMODIUM SPP

SEQUENCE LISTING

Incorporated by reference in its entirety herein is a computer-readable nucleotide/amino acid sequence listing submitted concurrently herewith and identified as follows: One 1,159 Byte ASCII (Text) file named "10569703_ST25.TXT," created on Apr. 6, 2007.

FIELD OF THE INVENTION

THIS INVENTION relates to an immunogenic agent and pharmaceutical composition, in particular an immunotherapeutic composition, preferably a vaccine against one or more different strains or species of pathogen. The immunotherapeutic composition is particularly useful for stimulating a cellular immune response for reducing severity of infection and/or improving treatment and recovery from infection from a pathogen such as *Plasmodium* spp.

BACKGROUND OF THE INVENTION

Diseases have plagued animals, including humans, for centuries. Modern medicine has successfully developed vaccines for some diseases, for example polio, thereby providing protection against infection by some disease causing pathogens. Such vaccines have improved human health and potentially save millions of lives annually. However, developing vaccines to protect against infection by some pathogens has proven to be challenging and remains elusive. For example, malaria vaccines against *Plasmodium* species and different strains thereof are yet to be successful.

Early attempts to develop a malaria vaccine include irradiated sporozoites that are live, but inactived or attenuated, (i.e. are capable of infecting, but not replicating in a host), Clyde 1975, Am J Trop Med Hyg 24 397. Delivery of this type of vaccine commonly relied on the attenuated live sporozoites being inoculated through mosquito bites, see Herrington et al, 1990, Bull World Health Organ. 68 Suppl 33. This type of vaccine is difficult to implement and has not resulted in a successful malaria vaccine.

Recently, a common approach in developing a vaccine is identification of a pathogen antigen, cloning of the nucleic acid encoding the antigen and protein expression of recombinant nucleic acid. This approach for developing a malaria vaccine has resulted in a number of blood-stage derived recombinant antigens for inclusion in subunit vaccines, including MSP1, MSP2, MSP3, MSP4, MSP5, AMA1, PfEMP1, RESA, RAP1, and RAP2 (Carvalhuo et al, 2002, Scand J. Immol 56 327). However, a subunit vaccine for malaria is yet to be successful.

Although subunit vaccines are the most common form of a malaria vaccine currently in development, a subunit vaccine has a number of limitations, in particular in relation to developing a vaccine against a pathogen characterised by multiple strains, for example *Plasmodium*. An important inadequacy of subunit vaccines is their aim to mimic natural immunity, a process that in itself may be entirely inadequate. This is illustrated, for example, from a study conducted in Kenya (Hoffman et al, 1987, Science 237 639). The researchers treated adult Kenyan volunteers who had lived their entire lives in a malaria endemic area with anti-malaria drugs and then monitored each volunteer for appearance of *Plasmodium* parasites in their blood over the ensuing three months. By three months, 80% of the volunteers had become infected with *Plasmodium* parasites although antibody levels against the pathogen circumsporozoite protein were indistinguishable between individuals who developed parasitemia and those who did not. Thus, immunity to sporozoites (the form of the parasite inoculated by the mosquito) was inadequate, immunity to liver stage parasites (the next stage in the life cycle) was inadequate and immunity to blood forms (the stage of exponential growth after the liver stage) was also inadequate.

Subunit vaccines that aim to mimic natural immune responses by inducing antibodies to the sporozoite coat, by inducing T cells which secrete INF-γ (gamma interferon) and which are potentially cytolytic for infected liver cells or inducing antibodies to merozoite surface proteins to block the invasion of red blood cells have not provided protection against malaria. There are three main possibilities why naturally occurring immune responses induced by subunits are not protective: (i) small molecules lack sufficient immunological determinants (or epitopes) to be widely immunogenic; (ii) many malaria proteins, and all major vaccine candidates, are polymorphic and these polymorphisms can be discriminated by antibodies or T cells raised against any one particular polymorphism; and (iii) malaria infection suppresses the induction of immunity by blocking dendritic cell maturation (Urban et al, 1999, Nature 400 73) and killing parasite-specific T cells by apoptosis (Xu et al, 2002, J Exp Med 195 881) and thus prevents the development of antibody-independent immunity as well as T cell-dependent antibody responses and subsequent memory responses.

It was recently shown that it was possible to immunize humans against a single strain of *Plasmodium* using an ultra-low dose of live *P. faiciparum* infected red blood cells (Pombo et al, 2002, Lancet 360 610). In this study, naive volunteers were repeatedly infected with parasites and drug treated to stop the infection. They did not develop any symptoms of malaria during the eight days during which parasite numbers increased as determined by a very sensitive Polymerase Chain Reaction (PCR). Parasites could not be detected by microscopy. Although immunisation with ultra-low dosages of live parasite may provide some protection against subsequent infection by the same parasite, it is difficult to cultivate large numbers of live parasite for use in a vaccine. Transport of live parasites to areas requiring administration of the vaccine, maintaining the parasites viability and a requirement for blood products to propagate live parasite for the vaccine is not practical and is prohibitive for general application. Areas affected by malaria are typically remote with limited facilities. Also, inoculation with live pathogen is cumbersome and requires repeated infection/treatment cycles to prevent full infection.

Rhee et al, 2002, J Exper Med 195 1565 describes vaccination of mice with heat killed *Leishmania major* and either IL-12 or CpG oligonucleotide (CpG-ODN). This publication relates to a specific pathogen, *Leishmania major*, which is the causative agent of cutaneous leishmaniasis and a vaccine for the same pathogen.

There is a need for a pharmaceutical composition capable of stimulating an immune response in an animal and reducing a risk of infection or improving recovery from an infection by one or more pathogen, namely *Plasmodium* spp or strain.

SUMMARY OF THE INVENTION

The inventors have developed a pharmaceutical composition that is suitable for inducing immunity against homologous and heterologous forms of a pathogen, e.g. one or more of a same or different species or strain of species. In a preferred form, the invention relates to a surprising discovery that administering an animal with a low dose of an antigenic component derived from a pathogen was capable of reducing an occurrence of pathogen infection in a same and different strain of pathogen. In particular, a preferred form of the invention relates to a composition and administration of the composition comprising a low dose of an antigenic component derived from at least one species of killed *Plasmodium*, which is capable of inducing an immune response for one or more strains of *Plasmodium*. Malaria is caused by one or more species of *Plasmodium* and each species of *Plasmodium* comprises potentially hundreds, if not thousands of identified and unidentified strains, making development of a successful pharmaceutical composition for preventing or treating malaria difficult. The present discovery provides a means for practically developing a pharmaceutical composition that when administered is preferably capable of inducing an immune response in an animal against one or more strains of *Plasmodium* spp.

The background art does not describe this surprising discovery and a pharmaceutical composition comprising this preferred characteristic is only now possible or contemplated by the present invention.

As will be described herein in more detail, the low dose of an antigenic component from a pathogen may be administered in combination with other agents, including an agent capable of increasing IL-12 in an animal, such as a CpG nucleic acid, and an adjuvant such as alum.

In a first aspect, the invention provides an immunogenic agent comprising:

a low dose of an antigenic component obtainable from at least one *Plasmodium* spp; and an agent capable of increasing an amount of IL-12 in an animal.

Preferably, the antigenic component is selected from the group consisting of: live whole *Plasmodium* spp, inactivated whole *Plasmodium* spp, killed whole *Plasmodium* spp, an extract from *Plasmodium* spp, purified proteins derived from *Plasmodium* spp, one or more recombinantly expressed nucleic acid encoding *Plasmodium* spp proteins and a pool of recombinant expressed *Plasmodium* spp proteins.

More preferably, the antigenic component comprises an extract from one or more different species of killed *Plasmodium* spp.

Preferably, the extract comprises an equivalent of less than $10^6$ whole *Plasmodium* spp.

More preferably, the extract comprises an equivalent of less than $10^5$ whole *Plasmodium* spp.

Even more preferably, the extract comprises an equivalent of less than $10^3$ whole *Plasmodium* spp.

In one form, the extract may comprise an equivalent of less than $10^2$ and even less than 10 whole *Plasmodium* spp.

*Plasmodium* spp is preferably selected from the group consisting of: *Plasmodium falciparum, Plasmodium vivax, Plasmodium malariae, Plasmodium ovale, Plasmodium knowlesi, Plasmodium berghei, Plasmodium yoelii, Plasmodium chabaudi* and *Plasmodium vinckei*.

Preferably, the at least one *Plasmodium* spp is selected from the group consisting of: *Plasmodium falciparum, Plasmodium vivax, Plasmodium malariae* and *Plasmodium ovale*.

Preferably, the *Plasmodium* spp is *Plasmodium falciparum*.

In one form of the first aspect, the agent capable of increasing an amount of IL-12 in the animal is capable of stimulating endogenous IL-12 expression in the animal.

More preferably, the agent comprises a CpG nucleic acid.

Preferably, the CpG nucleic acid comprises a nucleotide sequence selected from the group consisting of:

```
TCGTCGTTTTGTCGTTTTGTC,      (SEQ ID NO: 1)

TCCATGACGTTCCTGACGTT        (SEQ ID NO: 2)
and

TCCAGGACTTCTCTCAGGTT.       (SEQ ID NO: 3)
```

In another form of the first aspect, the agent capable of increasing an amount of IL-12 in the animal is IL-12 protein or biologically active fragment thereof.

Preferably, the IL-12 protein or biologically active fragment thereof is human IL-12.

In one form, the IL-12 protein or biologically active fragment thereof is recombinant the IL-12 protein or biologically active fragment thereof.

In another form, the IL-12 protein or biologically active fragment thereof is isolated wild type IL-12 protein or biologically active fragment thereof.

In another form of the first aspect, the agent capable of increasing an amount of IL-12 in the animal is a nucleic acid comprising a nucleotide sequence encoding IL-12 protein or biologically active fragment thereof.

Preferably, the nucleic acid is operably linked to a promoter capable of expressing the nucleic acid in the animal.

The immunogenic agent preferably further comprises an adjuvant.

Preferably, the adjuvant is selected from the group consisting of: aluminum hydroxide (alum), IL-12, CpG-oligonucleotide (ODN), SBAS2, SBAS4, QS21 and ISCOMs In a more preferred form, the adjuvant is aluminum hydroxide.

Preferably, the animal is a mammal.

More preferably, the mammal is human.

In a second aspect, the invention provides a pharmaceutical composition comprising the immunogenic agent of the first aspect and a pharmaceutically-acceptable carrier.

Preferably, the pharmaceutical composition is an immunotherapeutic composition.

More preferably, the immunotherapeutic composition is a vaccine.

Preferably, the pharmaceutical composition, which when administered to the animal is capable of reducing severity of or improving recovery from infection by one or more different *Plasmodium* spp.

Preferably, the one or more different *Plasmodium* spp comprises one or more respective stains thereof.

Preferably, the vaccine is capable of providing protective immunity in a mammal against one or more different *Plasmodium* spp.

Preferably, the one or more different *Plasmodium* spp comprises one or more respective stains thereof.

In a third aspect, the invention provides a method for inducing an immune response in an animal, including the step of administering the pharmaceutical composition of the second aspect to a mammal.

Preferably, the pharmaceutical composition is an immunotherapeutic composition capable of reducing severity of infection by or improving recovery from infection by *Plasmodium* spp in the mammal.

Preferably, the immunotherapeutic composition is a vaccine capable of providing protective immunity or treating the mammal against one or more *Plasmodium* spp.

The mammal is preferably human.

In a fourth aspect, the invention relates to use of the pharmaceutical composition of the second aspect to reduce severity of infection by or improve recovery from infection by *Plasmodium* spp in the animal.

Preferably, use of the pharmaceutical composition prevents or treats *Plasmodium* spp infection in the animal.

Preferably, the animal is a mammal.

More preferably, the mammal is human.

Preferably, use of the pharmaceutical composition reduces severity of by or improves recovery from malaria.

More preferably, use of the pharmaceutical composition of prevents or treats malaria.

It will be appreciated that the present invention provides a pharmaceutical composition and method capable of reducing a risk of infection and/or improving recovery from an infection from a pathogen. In a preferred form of the invention, the pharmaceutical composition is an immunotherapeutic composition capable of inducing an immune response in an animal administered with the immunotherapeutic composition. In an even more preferred form, the invention is a vaccine capable of providing protection against a pathogen, in particular intracellular pathogens comprising a plurality of strains or variants characterized by heterogeneous antigens. More particularly, the present invention is preferably capable of inducing and maintaining a cellular immune response in an animal, namely a human, against one or more strains of *Plasmodium* spp, the causative agent of malaria. Accordingly, preferred forms of the invention relate to a pharmaceutical composition comprising an antigenic component from at least one species of *Plasmodium* spp capable of infecting a human, e.g. *P. falciparum, P. vivax, P. malariae* and *P. ovale*, and use of the pharmaceutical composition to prevent malaria in a human.

Throughout this specification unless the context requires otherwise, the word "comprise", and variations such as "comprises" or "comprising", will be understood to imply the inclusion of the stated integers or group of integers or steps but not the exclusion of any other integer or group of integers.

BRIEF DESCRIPTION OF THE FIGURES AND TABLES

In order that the invention may be readily understood and put into practical effect, preferred embodiments will now be described by way of example with reference to the accompanying figures and tables.

FIG. 1: Levels of malaria-specific antibodies in the sera of A/J mice immunized s.c. with antigen alone, antigen in alum, antigen plus IL-12 or antigen plus IL-12 in alum and boosted 3 weeks later by i.p. injection with antigen. Two weeks later, sera were collected from immunized mice and the levels of total malaria-specific antibody, IgG1, and IgG2a were determined by ELISA. Data represent OD values for individual mice and are pooled from 2 experiments.

Figure 2:
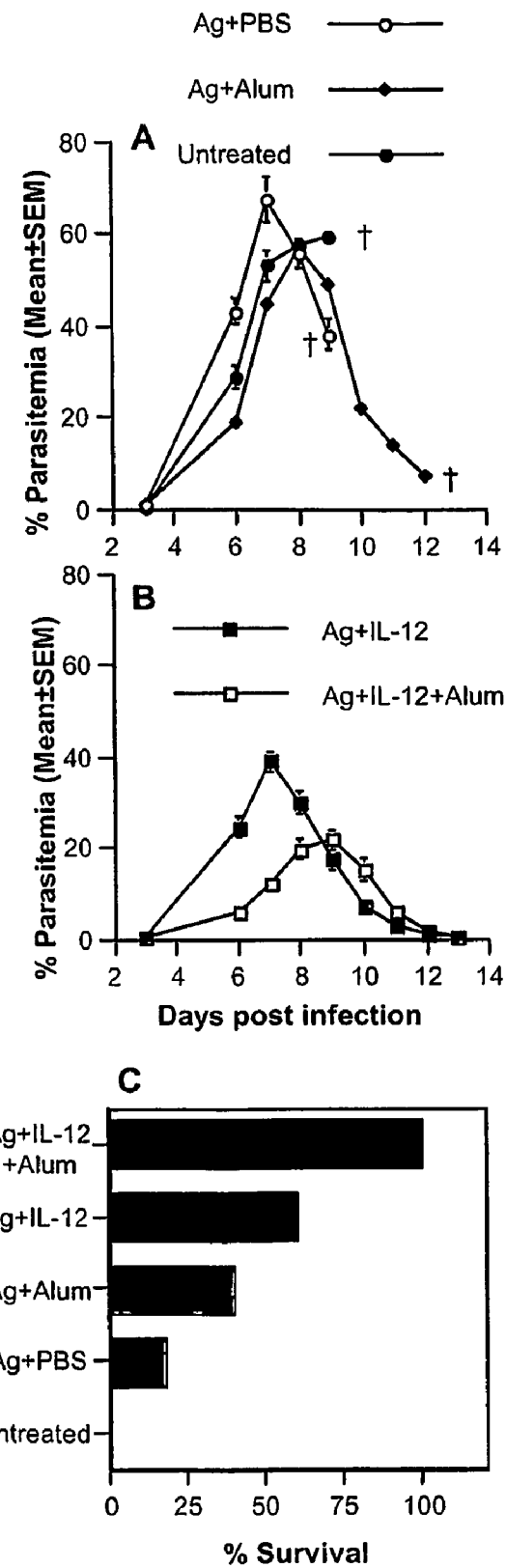

FIG. 2: Course of parasitemia and survival in A/J mice immunized s.c. with antigen alone, antigen in alum, antigen plus IL-12, or antigen plus IL-12 in alum and boosted 3 weeks later by i.p. injection with antigen. Two weeks later, immunized and untreated, control mice were challenged i.p. with $1 \times 10^6$ *P. chabaudi* AS parasitized red blood cells (PRBC). The percentage of PRBC in peripheral blood (A and B) was determined for each group of 5 mice. Data of one of two replicate experiments are presented. Mice were examined twice daily for the duration of the experiment for survival (C). Cumulative data from 6 experiments are shown.

Figure 3:
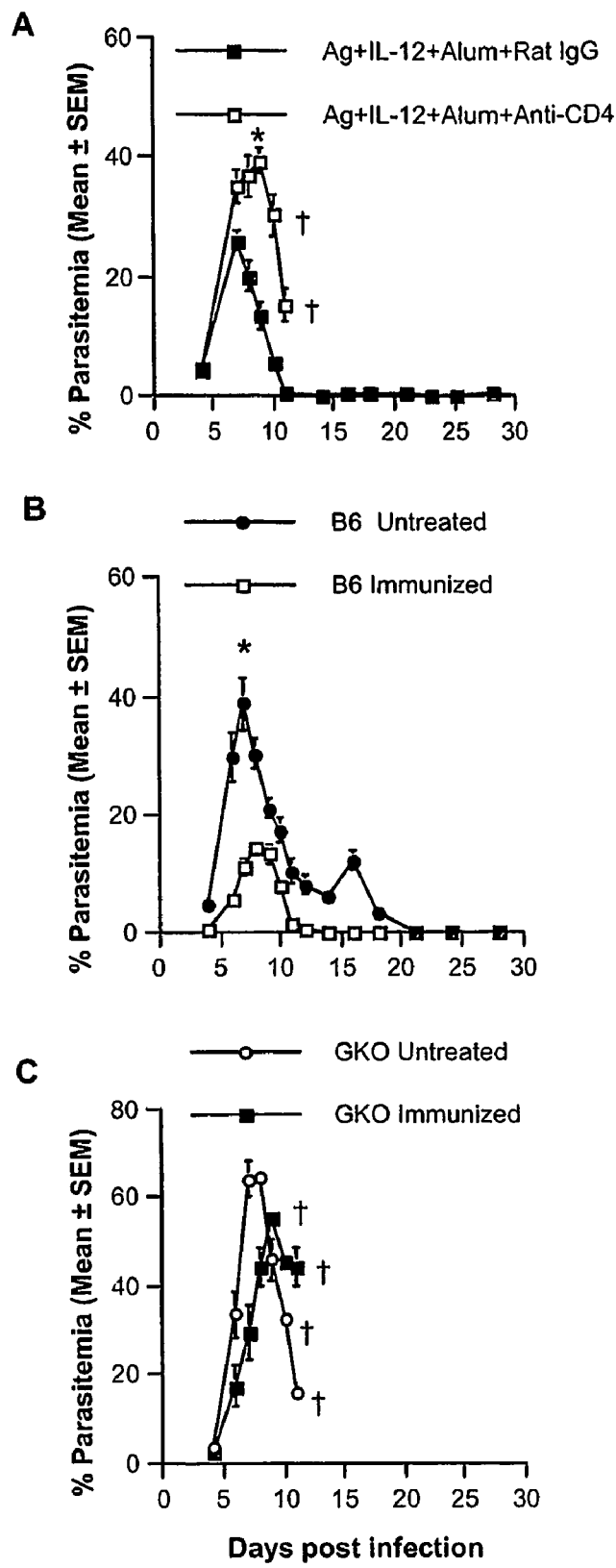

FIG. 3: Course of parasitemia and survival in immunized CD4+T cell depleted A/J mice or in wildtype or IFN-γ deficient (GKO) C57BL/6 mice. To deplete CD4+ in vivo, A/J mice were treated i.p. with GK1.5 monoclonal antibody or with an equivalent amount of rat IgG as control 3 days prior to challenge infection and three times per week during infection. Two weeks after boosting, mice were challenged i.p. with $1 \times 10^6$ *P. chabaudi* AS PRBC and the course of parasitemia was determined (A). Female wildtype (B) and GKO (C) C57BL/6 mice were immunized with antigen plus IL-12 in alum and two weeks after boosting, mice were challenged i.p. with $1 \times 10^6$ *P. chabaudi* AS PRBC and the course of parasitemia was determined. Similar results were obtained in a replicate experiment using male wildtype and GKO mice. In panel A, *, p<0.001, for control vs. CD4+T cell depleted mice. In panel B, *, p<0.0001, for untreated vs. immunized C57BL/6 mice.

Figure 4:
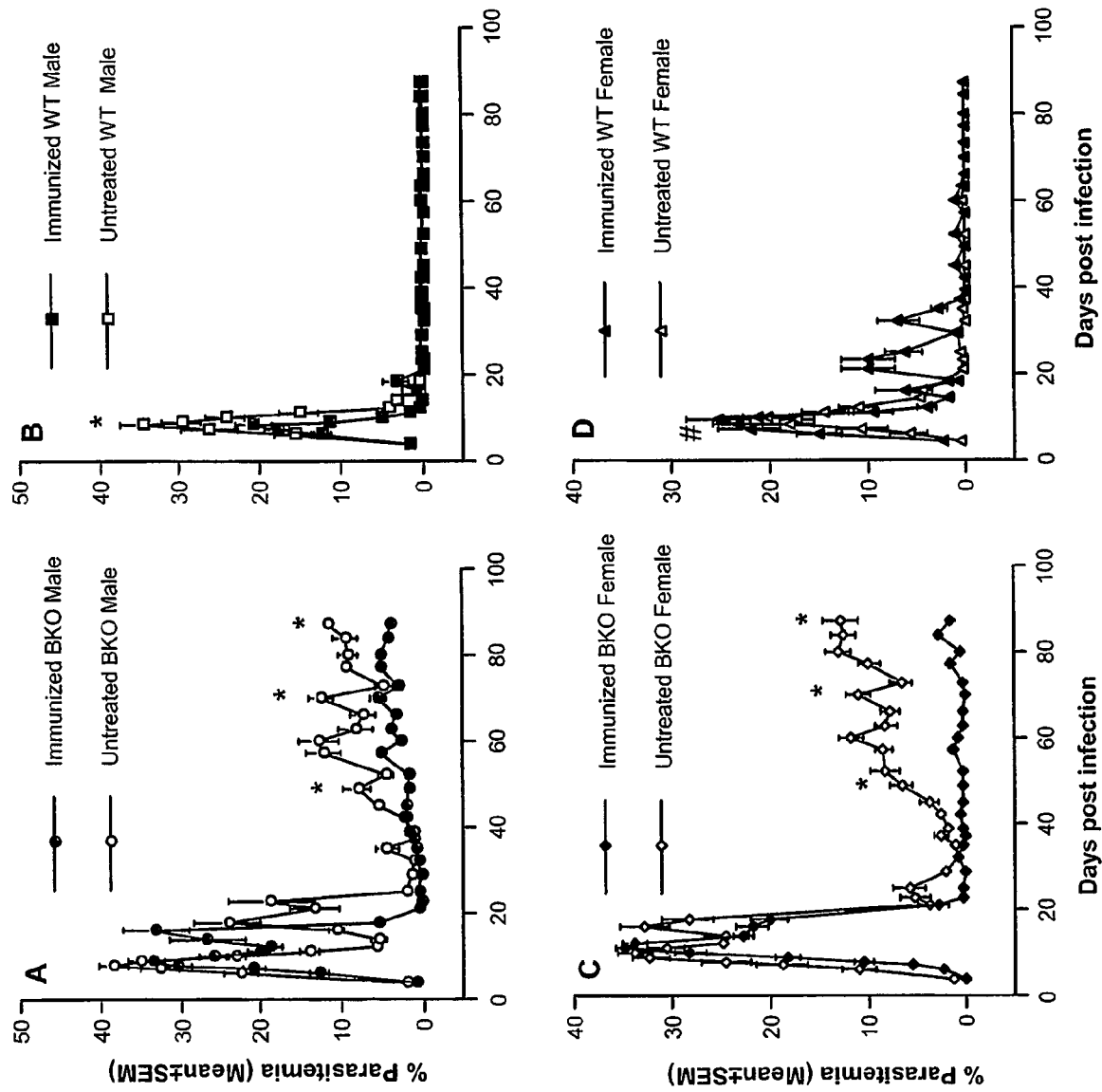

FIG. 4: Course of parasitemia in immunized B cell-deficient μ-MT (BKO) and wildtype (WT) C57BL/10 mice. Groups of BKO (male, n=6; female, n=8) and WT (male and female, n=10) mice were immunized s.c. with antigen plus IL-12 in alum and boosted i.p. with antigen three weeks later. Two weeks later, mice were challenged i.p. with $1 \times 10^6$ *P. chabaudi* AS PRBC and the course of parasitemia was determined in male (A, B) and female (C, D) BKO (A, C) and wildtype (B, D) mice. *, p<0.001, #, P<0.05 for unimmunized vs. immunized mice.

Figure 5:
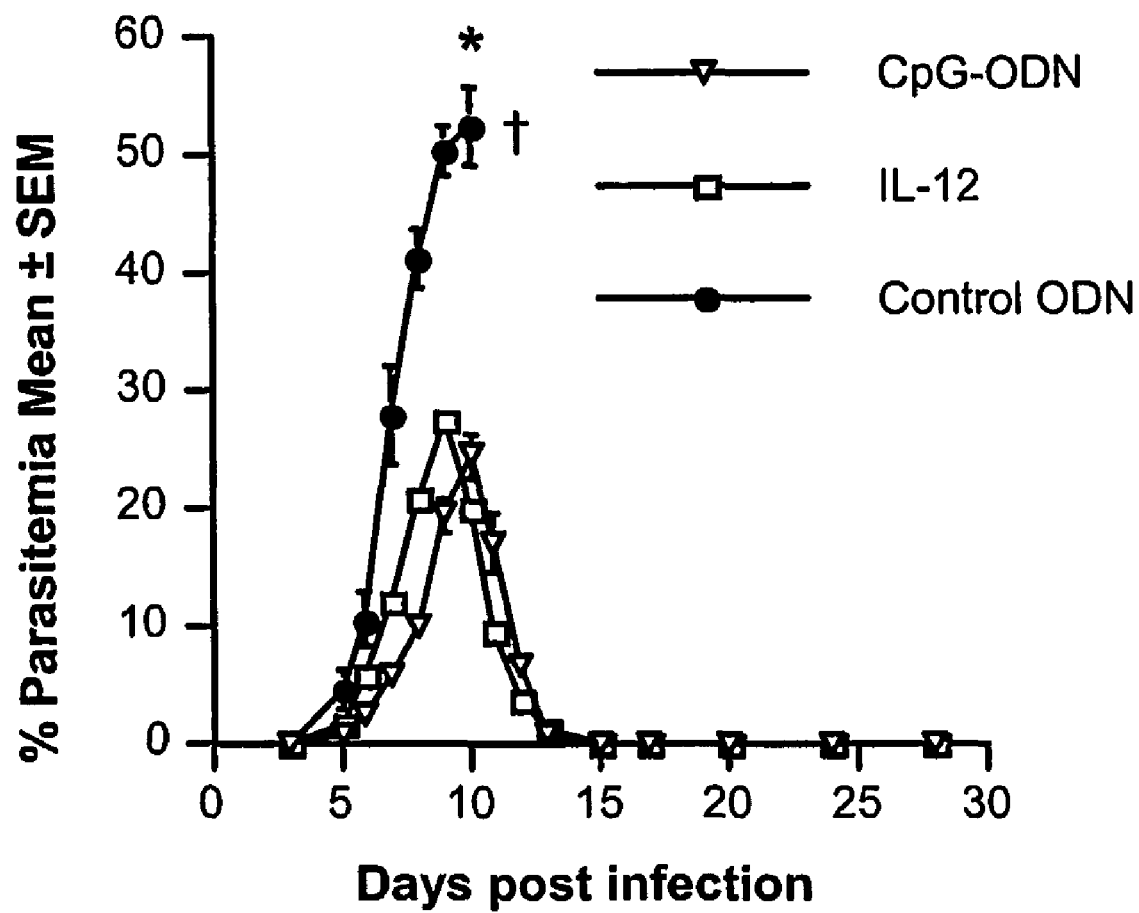

FIG. 5: Course of parasitemia in A/J mice immunized with antigen plus IL-12 in alum or antigen plus CpG-ODN in alum. Groups of 5 A/J mice were immunized s.c. with either antigen plus IL-12 in alum (IL-12), antigen plus CpG-ODN in alum (CpG-ODN), or antigen plus ODN in alum (Control ODN) and boosted i.p. with antigen three weeks later. Two weeks later, mice were challenged i.p. with $1 \times 10^6$ *P. chabaudi* AS PRBC and the course of parasitemia was determined. *, p<0.001 for day 9 parasitemia between antigen plus ODN in alum versus antigen plus CpG-ODN in alum. p=0.114 for antigen plus CpG-ODN in alum versus antigen plus IL-12 in alum.

Figure 6:
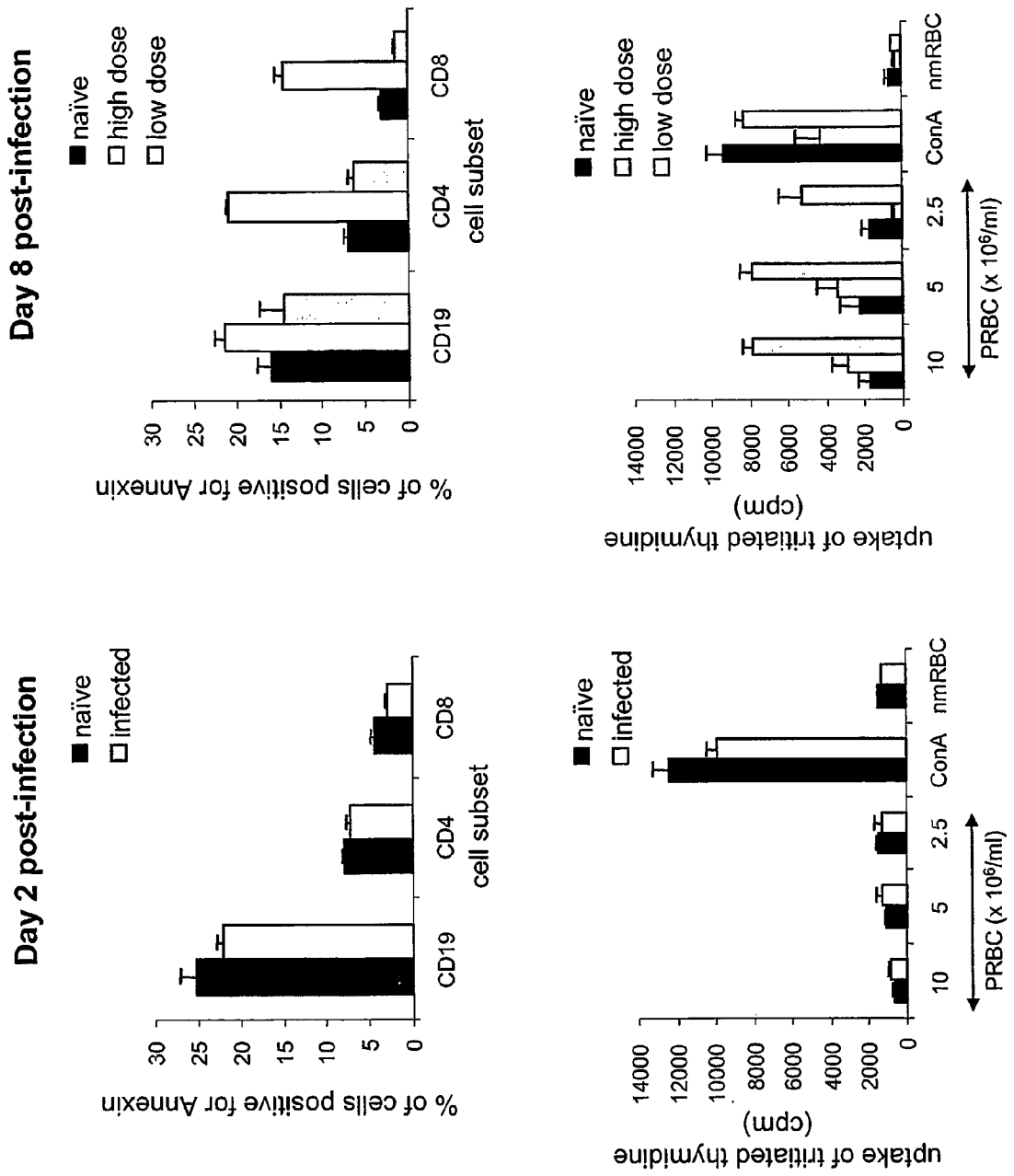

FIG. 6: A single low dose infection primes antigen-specific splenic lymphocytes without inducing lymphocyte apoptosis. Mice were infected with $1 \times 10^5$ *P.c.chabaudi* AS PRBC i.v. at day 0. On day 2, a first group of infected mice was killed along with naïve controls (n=4). Low dose mice were drug-cured on day 2, while high dose mice were allowed to develop detectable parasitaemia. Naïve, high dose and low dose mice were killed at day 8 (n=4). Apoptosis of splenic lymphocyte subsets was assessed by staining with Annexin V and antigen-specific proliferation of lymphocytes was examined. Means+SEM are shown. This is representative of two experiments.

Figure 7:
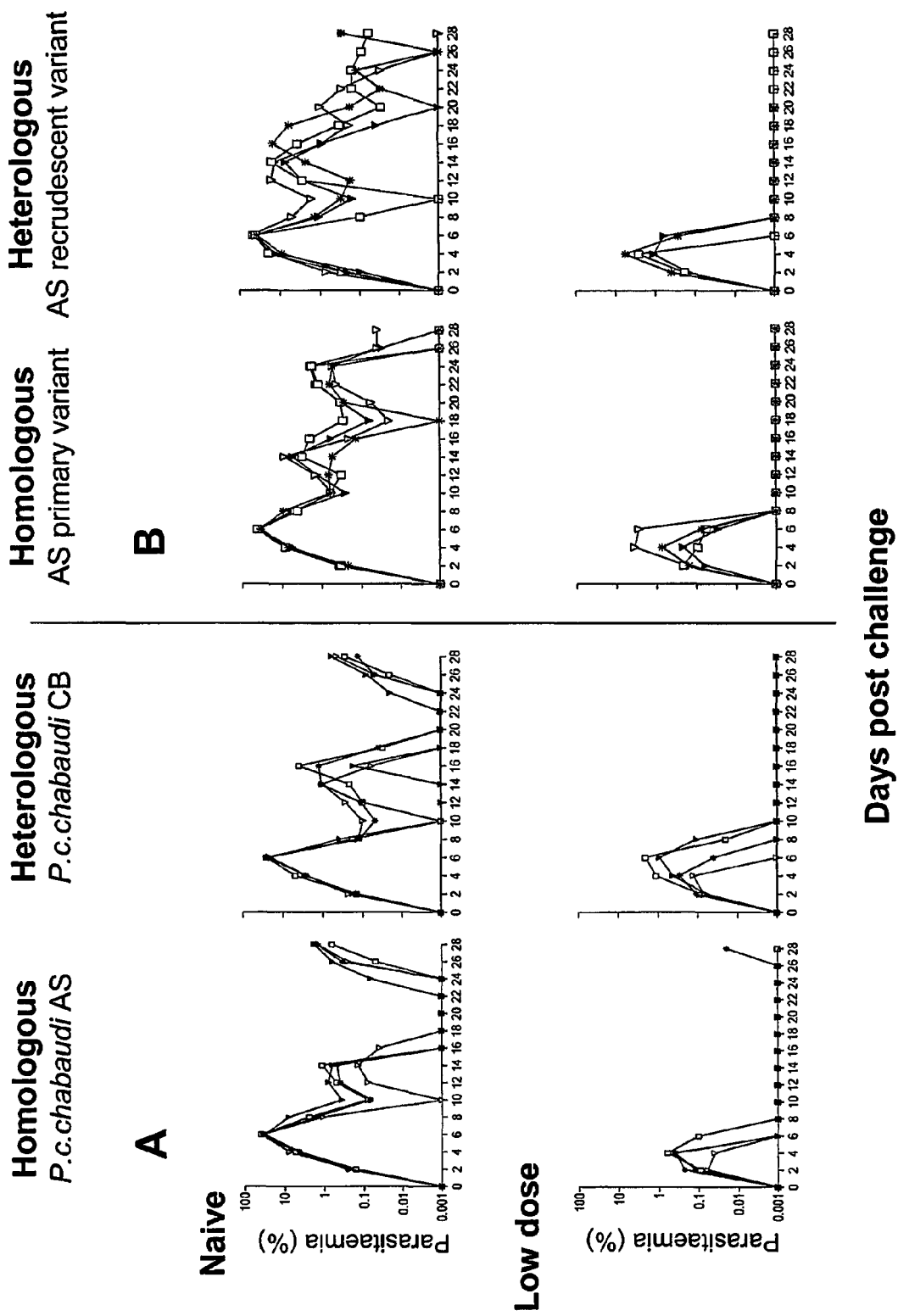

FIG. 7: Low dose infection induced significant protection against challenge with homologous and heterologous parasites. Low dose mice (lower panels) were administered three i.v. injections at 3-4 week intervals with $1 \times 10^5$ *P.c.chabaudi* AS primary variant PRBC. Naïve mice (upper panels) were injected with PBS at the same time points. All mice were administered Malarone by oral gavage for four consecutive days, commencing 48 hours after each injection. Six weeks after a third injection mice were challenged i.v. with either (A) $1 \times 10^6$ *P.c.chabaudi* AS primary variant PRBC, $1 \times 10^6$ *P.c.chabaudi* CB PRBC or (B) $1 \times 10^6$ *P.c.chabaudi* AS recrudescent variant PRBC. Parasitaemia was monitored by blood smears for 4 weeks post-challenge. Each line represents an individual mouse.

Figure 8:
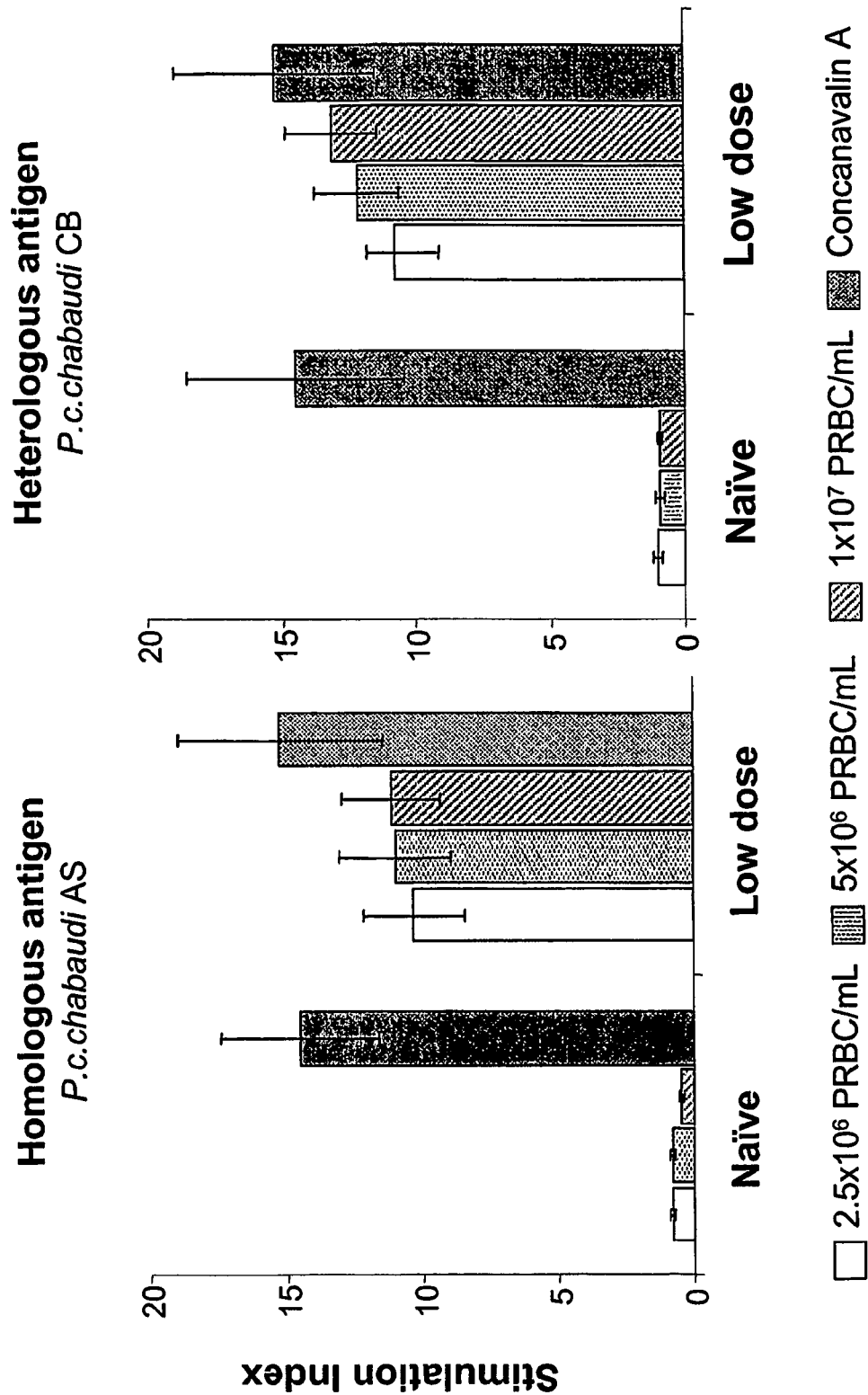

FIG. 8: Splenic lymphocytes from low dose mice showed significant proliferation in vitro to homologous and heterologous parasite antigen. Low dose mice were given three i.v. injections at 3-4 week intervals with $1 \times 10^5$ *P.c.chabaudi* AS primary variant PRBC. Naïve mice were injected with PBS at the same time points. All mice were administered Malarone by oral gavage for four consecutive days, commencing 48 hours after each injection. Spleens were removed 6 weeks after the third injection and single spleen cell suspensions cultured in vitro with nmRBC, Concanavalin A or different doses of homologous (*P.c.chabaudi* AS) or heterologous (*P.c.chabaudi* CB) PRBC. Results show an average stimulation index +/− standard error of 4 mice. The stimulation index is a ratio of proliferation in the presence of stimulant to proliferation in the presence of nmRBC. Values over three are typically regarded as significant. Data from one of three replicate experiments are presented.

Figure 9:
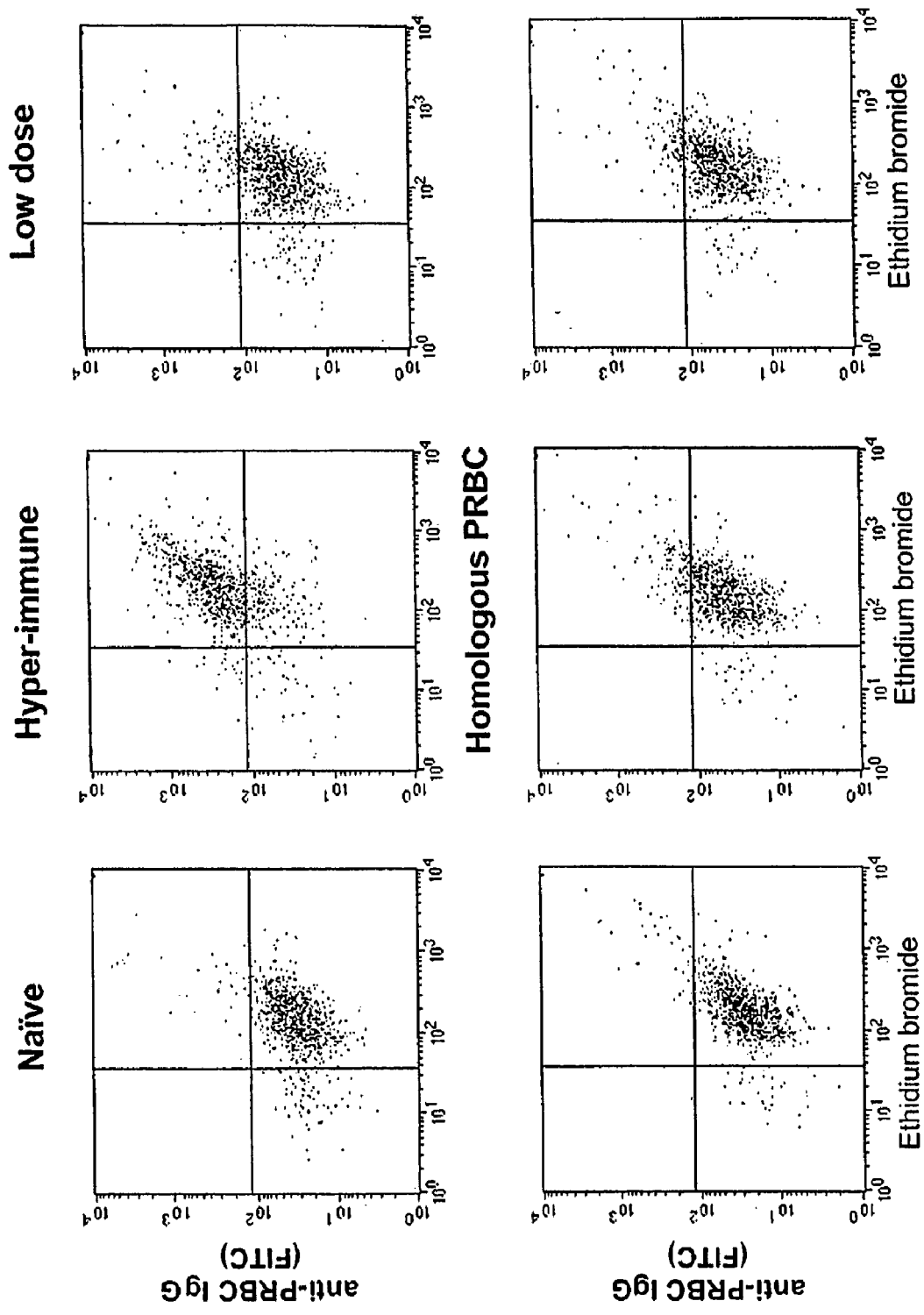

FIG. 9: Serum from low dose mice had significantly lower levels of IgG that bound strain-specific antigens on the surface of homologous PRBC compared to hyper-immune serum. Low dose mice were given three i.v. injections at 3-4 week intervals with $1 \times 10^5$ *P.c.chabaudi* AS primary variant PRBC. Naïve mice were injected with PBS at the same time points. All mice were given Malarone by oral gavage for four consecutive days, commencing 48 hours after each injection. Hyper-immune serum was generated by giving mice three i.v. injections at 3-4 week intervals with $1 \times 10^5$ *P.c.chabaudi* AS PRBC and allowing the mice to self cure, exposing the mice to high doses of live parasite. Serum was collected from all mice 3 weeks after the third injection. *P.c.chabaudi* AS (homologous) or *P.c.chabaudi* CB (heterologous) late stage PRBC were stained with serum indirectly conjugated to FITC to detect red cell surface antigens and the parasite DNA counterstained with ethidium bromide, which binds directly to the DNA. Cells were analysed by flow cytometry. Data show a representative mouse from each group of 10 from one of two replicate experiments. Numbers indicate percentage of cells in each quadrant.

Figure 10:
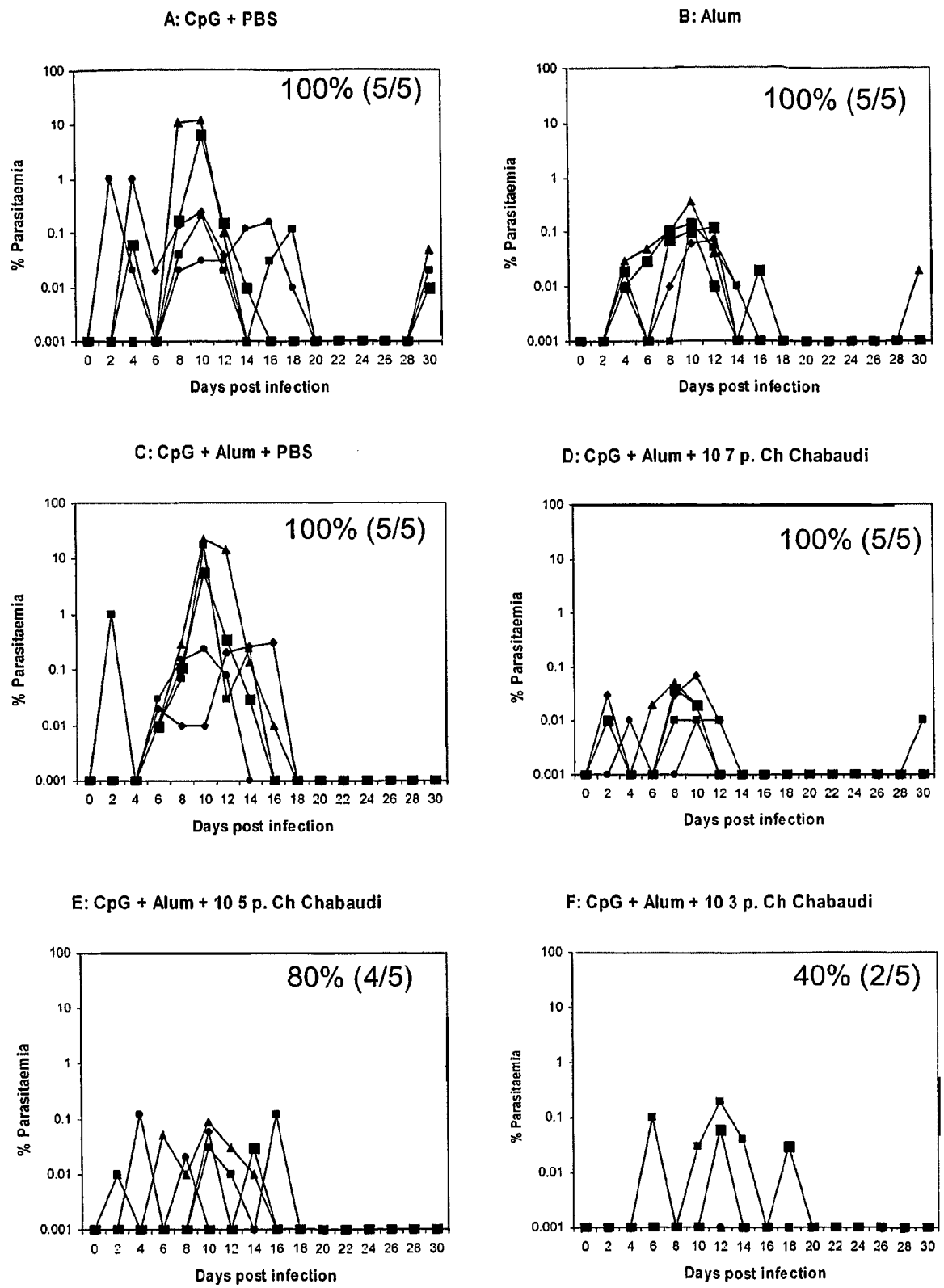

FIG. 10 shows a low dose ($1 \times 10^3$)), killed plasmodium parasite, in combination with CpG plus alum, induces significant protection against challenge with homologous parasite in A/J mice. Animals were first immunized subcutaneously with either CpG (Group A), alum (Group B), combined CpG plus alum, or combined CpG, alum and dead parasite ($1 \times 10^3$ (Group F), $1 \times 10^5$ (Group E) or $1 \times 10^7$ (Group D) *P.c.chabaudi* parasites (ip) that had been killed by multiple freeze/thaw cycles) at Day 0. At Day 21, animals were boosted with same amount of parasite or PBS alone (ip). At Day 42, mice were given a further boost with the same amount of dead parasite (ip). On Day 56, all animals were challenged with live $1 \times 10^5$ *P.c.chabaudi* parasites administered intraveneously. Parasitaemia was monitored by blood smears for 30 days post-challenge. Each line represents percent parasitaemia in an individual mouse (n=5 per group).

Figure 11:
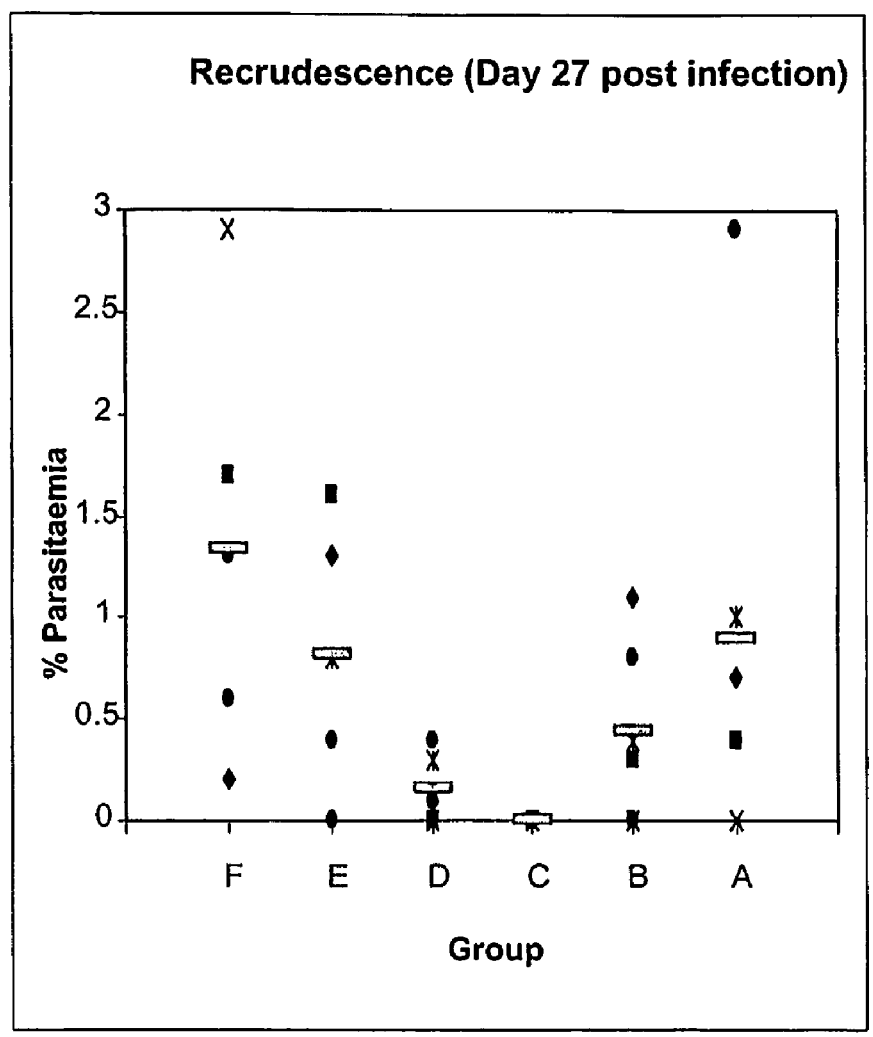

FIG. 11 shows low dose ($1 \times 10^3$ and $1 \times 10^5$) of heat-killed *plasmodium* parasite combined with CpG and alum, prevents recrudescence in C57BL/6 mice. Animals were immunized subcutaneously with either CpG (Group F), combined CpG plus alum (Group B, C, D, E), control (inactive CpG) plus alum (Group A), or combined CpG, alum and dead parasite ($1 \times 10^3$ (Group F), $1 \times 10^5$ (Group E), or $1 \times 10^7$ (Group D) *P.c.chabaudi* parasites) at Day 0. At Day 21, animals were boosted the same amount of dead parasite or vehicle alone. At Day 42, all animals were challenged with live $1 \times 10^5$ *P.c.chabaudi* parasites administered intraveneously. Parasitaemia was monitored by blood smears for 30 days post-challenge. Each data point represents % parasitaemia in an individual mouse (n=5 per group). Straight bars represent the mean data of n=5 animals per group. A=Control CpG+Alum+$10^7$ *p. Ch. Chabaudi*; B=CpG+Alum+$10^7$ *p. Ch. Chabaudi*; C=CpG+Alum+$10^5$ *p. Ch. Chabaudi*; D=CpG+Alum+$10^3$ *p. Ch. Chabaudi*; E=CpG+Alum+PBS; F=CpG+PBS TABLE 1: Antigen-Specific Spleen Cell Proliferation and Cytokine Responses in Immunized Mice Prior to *P. chabaudi* AS Challenge Infection.

TABLE 2: Long Term Protection Against Blood-Stage Malaria Induced by Immunization With Malaria Antigen Plus IL-12 in Alum.

DETAILED DESCRIPTION OF THE INVENTION

Unless defined otherwise, all technical and scientific terms used herein have a meaning as commonly understood by those of ordinary skill in the art to which the invention belongs. Although any method and material similar or equivalent to those described herein can be used in the practice or testing of the present invention, preferred methods and materials are described. For the purpose of the present invention, the following terms are defined below.

The present invention relates to a pharmaceutical composition that is preferably capable of inducing heterologous immunity against a pathogen. Accordingly, the pharmaceutical composition preferably comprises an immunotherapeutic agent capable of inducing an immune response in an animal. The immunotherapeutic agent is preferably capable of is of reducing infection and/or improving recoverfrom infection by *Plasmodium* species. The invention in a preferred form may be useful for protection against different, but preferably related, pathogens. A preferred pathogen described herein is *Plasmodium*, which is known to comprise different species and strains or variants. In a preferred form, the pharmaceutical composition of the invention comprises a low dose of an antigenic component obtainable from at least one strain of *Plasmodium* and a CpG nucleic acid, IL-12 protein and/or nucleic acid encoding IL-12, and an adjuvant such as alum. Preferably, the antigenic component is obtained from at least one species of *Plasmodium* capable of infecting a human that has been inactivated by killing.

Administration of a low dose respectively of live and killed parasite was investigated in the resistant mouse C57Bl/6 strain. The blood stage infection was restricted to levels undetectable on a blood smear by curative drug treatment 48 hours after infection in relation to administration of live *Plasmodium*. The investigators first determined that such a low dose infection was sufficient to prime lymphocytes whilst avoiding or minimising apoptotic death observed with a fulminant infection. The investigators then assessed an ability of multiple low dose infections to induce protective immunity following challenge infection with a high dose of either a homologous parasite or a heterologous parasite strain or variant. Initial investigations into the mechanism of protection found high levels of lymphocyte proliferation to both homolgous and heterologous parasite antigen and an absence of antibodies recognising antigens on the surface of PRBC.

The present invention also relates to the use of a low dose of an antigenic component from one or more *Plasmodium* spp in combination with an agent capable of increasing IL-12 in an animal, for example an agent capable of stimulating endogenous IL-12 expression in the animal and/or exogenous IL-12 in a pharmaceutical composition, immunotherapeutic composition or vaccine against *Plasmodium* spp. CpG-oligonucleotides are referred to herein as an agent capable of increasing IL-12 in an animal by stimulating endogenous IL-12 expression in the animal.

It will be appreciated that any suitable biologically active IL-12 may be used, for example a biologically active fragment of IL-12, IL-12 derived from any suitable source (including human and human orthologues, homologues, recombinant IL-12), nucleic acids and nucleic acid homologs encoding IL-12 (including nucleic acids encoding human IL-12, human IL-12 homologues and orthologues and homologous having one or more codon sequence altered by taking advantage of codon sequence redundancy). Preferably, the IL-12 administered to an animal is IL-12 protein or nucleic acid encoding IL-12 of the species of the animal. Accordingly, use of IL-12 in humans is preferably human IL-12 or biologically active fragment thereof.

Antigens and Pathogens

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material includes material in native and recombinant form. For example, isolated whole pathogen, extracts of a pathogen, purified proteins, recombinantly expressed proteins, including IL-12.

An "antigenic component" is meant a component derived from an organism capable of stimulating an immune response in an animal, preferably a mammal including mouse and human. An antigenic component may be an immunogenic agent. The antigenic component may comprise sub-cellular components including, organelles, membranes, proteins, lipids, glycoproteins and other components derived from the organism. The antigenic component may be derived from a whole organism, for example a whole parasite, or a part of an organism, for example a cell or tissue of an organism. The antigenic component may also include isolated sub-cellular components recombined, for example, respective membranes, proteins, lipids and glycoproteins may be purified and recombined. Also, a sub-set of proteins may be purified, for example by size fractionation or affinity purification, and recombined.

Further, the antigenic component may comprise one or more recombinantly expressed antigens. For example, an expression library, such as a cDNA library, may be prepared from an organism and encoded proteins recombinantly expressed. Suitable methods for preparing such an expression library are well known in the art and described for example in CURRENT PROTOCOLS IN MOLECULAR BIOLOGY Eds. Ausubel et al., (John Wiley & Sons, Inc. 1995-1999), in particular chapters 5 and 6, incorporated herein by reference. It will be appreciated that the antigenic component preferably comprises a plurality of antigens expressed by the organism, more preferably a majority of the antigens expressed by the organism, including greater than 50%, greater than 60%, greater than 75%, greater than 90%, greater than 95% and even greater than 99% and even 100% (for example whole extract or whole intact organism). It will be appreciated that in one form of the invention, the antigenic component need not be fully characterized and specific antigens of the antigenic component may not be defined. This has advantages in that time and effort is not required to isolate and purify specific and defined antigens. In one form of the invention, a crude extract of the pathogen may be used.

In a preferred form, the antigenic component comprises live *Plasmodium* spp, inactivated *Plasmodium* spp, killed *Plasmodium* spp, extract derived from the *Plasmodium* spp, purified proteins derived from the *Plasmodium* spp, recombinantly expressed nucleic acids encoding proteins derived from the *Plasmodium* spp and a pool of recombinant expressed proteins derived from the *Plasmodium* spp. In a preferred form, the antigenic component is a *Plasmodium* spp that has been killed, for example by freezing and thawing, and is not able to infect a host. In contrast, an inactivated *Plasmodium* spp comprises attenuated *Plasmodium* spp that are capable of infecting, but not replicating, in a host. A preferred species of *Plasmodium* is one that is capable of infecting humans, for example *Plasmodium falciparum, Plasmodium vivax, Plasmodium malariae* or *Plasmodium ovale*.

An antigenic component preferably comprises one or more antigens derived from one or more different pathogens, however, in one form of the invention, the antigenic component may comprise antigens derived from a single pathogen, for example, a single species of *Plasmodium* or a single strain of a single species of *Plasmodium*. The pathogen preferably comprises one or more different *Plasmodium* spp, including for example *P. falciparum, P. vivax, P. malariae, P. ovale, P. knowlesi, P. berghei, P. yoelii, P. chabaudi* and/or *P. vinckei*. In a preferred form, the antigenic component comprises all *Plasmodium* spp known to infect humans, namely one or more *Plasmodium* spp selected from the group consisting of: *Plasmodium falciparum, Plasmodium vivax, Plasmodium malariae* or *Plasmodium ovale*. The antigenic component may also comprise one or more strains of any one or more of the different *Plasmodium* spp. In a preferred form of the invention, the antigenic component comprises at least one strain of *Plasmodium* for each species capable of infecting a human, whereby heterologous immunity is provided for each strain of human *Plasmodium* spp when administered to a human. This is particularly advantageous as it will be appreciated there is potentially hundreds if not thousands of strains of *Plasmodium* capable of infecting humans, both known and unknown.

The antigenic component may comprise *Plasmodium* in any developmental form or combination thereof, including: sporozoites, merozoites, gametocytes and/or ookinetes. In a preferred form of the invention, the antigenic component is obtained from *Plasmodium* spp in the form of at least a merozoite. In a more preferred form, the *Plasmodium* spp is in the form of a merozoite.

It will also be appreciated that the antigenic component of the invention, when administered to a subject preferably reduces infection or improves recover from infection from one or more species and strains of *Plasmodium*. Accordingly, in a preferred form of the invention, administering to a human a pharmaceutical composition comprising an antigenic component from one or more different *Plasmodium* spp capable of infecting a human is capable of reducing or preventing malaria or improves recovery therefrom.

An antigenic component is suitably an immunogenic agent and included as an active in a pharmaceutical composition. In one preferred form of the invention, the antigenic component is included as part of an immunotherapeutic composition. In more preferred form of the invention, the antigenic component forms part of a vaccine. An ability of the antigenic component to stimulate an immune response preferably encompasses stimulation of at least a T-cell response. Stimulating an immune response in an animal may also be referred to as a "biological activity" of the antigenic component. In one preferred form, the antigenic component may stimulate a T-cell response without stimulating B-cells to produce antibodies capable of binding the antigenic component. In one form, a B-cell is not stimulated to produce antibodies, but may be activated to perform other known B-cell functions such as secreting cytokines.

"Extract" as used herein comprises the contents of a whole organism, fractions and sub-fraction of an extract, antigenic component of the organism and isolated component thereof.

By "endogenous" substance or compound is meant a substance or compound that may be found in a native cell, tissue or animal in isolation or otherwise. For example, endogenous IL-12 may be induced by CpG nucleic acid.

By "heterologous" pathogens means related pathogens that may be different strains or variants of a same or related species. An example of different strains of a same species is $P.\ c.\ chabaudi$ AS and $P.\ c.\ chabaudi$ CB. Heterologous may also refer to related species for example, $P.\ falciparum$ and $P.\ vivax$.

A "pathogen" as used herein refers to an agent capable of causing disease, for example a virus, bacteria, fungus or parasite. Parasite includes intracellular parasites such as $Mycobacterium$ spp, $Plasmodium$ spp and $Leishmania$ spp.

"$Plasmodium$ spp" as used herein comprises all $Plasmodium$ species, strains and variants, including: $P.\ falciparum, P.\ vivax, P.\ malariae, P.\ ovale, P.\ knowlesi, P.\ berghei, P.\ yoelii, P.\ chabaudi, P.\ c.\ chabaudi$ AS, $P.\ c.\ chabaudi$ CB and $P.\ vinckei$.

A strain of $Plasmodium$ spp includes variants within a same species, for example $P.\ c.\ chabaudi$ AS, $P.\ c.\ chabaudi$ CB. A variant is referred to in FIG. 7.

The term "low dose" is used herein to refer to a dose wherein an individual is infected or administered with a live (including inactivated and attenuated) or killed (e.g. dead) parasite, but the parasite density is preferably sufficiently low that the parasite cannot be substantially detected on a blood smear, more preferably no parasite can be detected. In relation to malaria, low dose is typically referred to as a subpatent infection. A low dose in a preferred form is capable of inducing a T-cell response when administered to an animal. Preferably, the low dose does not stimulate production of detectable antibodies from B-cells that are capable of binding to the antigenic component of the low dose.

A low dose of an antigenic component in a preferred form is derived from killed whole pathogen (for example killed whole $Plasmodium$ spp), wherein the dose is equivalent to less than $10^7$ whole pathogens/mL of blood from the animal, more preferably less than an equivalent of $10^6$, $10^5$, $10^4$, $10^3$, $10^2$ or 10 pathogens/mL of blood from the animal. An example of a low dose includes about 1000 to 3000 PRBC/mL of blood obtained from live PRBC, which have been treated to inactivate them, preferably by killing so that infection and replication in a host is not possible. Preferably, an equivalent of inactivated pathogen or antigenic component is prepared by calculating a number of parasite infected red blood cells (PRBC) in a sample and treating the PRBC to inactivate or kill the parasite and adjusting the concentration to achieve a desired blood concentration. For example, if a mouse is bled and $5\times10^8$ red blood cells are isolated at 20% parasitaemia, there is a total of $1\times10^8$ PRBC. The PRBC are lysed, sonicated and/or irradiated, which results in an amount of antigen equivalent to $1\times10^8$ PRBC. The sample comprising the parasite antigen(s) is diluted in an appropriate volume so that each recipient may be administered a dose of antigen equivalent to about preferably 1000-3000 PRBC/mL blood. An approximate volume of blood in a mouse is around 1 mL.

A person skilled in the art will appreciate that a low dose for administration in a human may be determined by administering an approximate low dose of antigenic component to a human and assessing an immune response in the human. Preferably, the immune response is characterised by inducing a T-cell response and preferably not inducing B-cells to produce detectable levels, or only low levels, of antibodies capable of binding to the antigenic component. A low level of antibody production preferably refers to a level not sufficient to protect an animal against a pathogen. A low dose is preferably less than an equivalent of $10^7$, $10^6$, $10^5$, $10^4$, $10^3$, $10^2$ or even less than 10 whole parasites. Accordingly, a low dose may comprise as few as an equivalent of 10, 50, 100, 200, 250, 500 or 750 whole parasite.

In one form of the invention, a preferred low dose for an antigenic component comprising one or more different species of $Plasmodium$ spp is less than an amount equivalent to $10^6$ parasite equivalents per mL of blood in the mouse. More preferably, less than an equivalent to $10^5$, $10^4$, $10^3$, $10^2$ or 10 parasite equivalents per mL of blood in the mouse. A preferred range is between an equivalent to $10^3$-$10^6$ parasite equivalents per mL of blood in the mouse. More preferably, the low dose is in a range between 10-$10^5$, more preferably in a range between $10^2$-$10^5$, even more preferably in a range between $10^3$-$10^4$. Preferably, the low dose is $1\times10^3$, $3\times10^3$, $5\times10^3$, $1\times10^4$, $5\times10^4$, $1\times10^5$, $5\times10^5$, $1\times10^6$, $5\times10^6$, $1\times10^7$ or $5\times10^7$ pathogens per mL of blood.

Also, an amount of the antigenic component of a low dose may be determined by a person skilled in the art by assessing an ability of the administered dose to provide partial or complete protection or recovery from a pathogen infection as describe herein. For example, providing partial or complete protection against malaria. Also, a low dose may be assessed by determining an ability of administration of the low dose of antigenic component to protect the animal against one or more different species or strains of pathogen, such as different species or strains of $Plasmodium$.

Proteins and Peptides

By "protein" is also meant "polypeptide", either term referring to an amino acid polymer, comprising natural and/or non-natural amino acids, D- or L-amino acids, as are well understood in the art. For example, IL-12 may be referred to as both a protein or polypeptide. "Protein" may refer to a peptide, polypeptide, or fragments thereof, inclusive of complexes with other moieties such as biotin, fluorochromes and nucleic acids. As described herein, proteins may be recombinantly expressed or isolated from a native source. Such proteins include pathogen proteins used in accordance with the present invention. For example, an extract in one form may comprise one or more proteins derived from one or more species of $Plasmodium$ spp.

In one embodiment, a "fragment" includes an amino acid sequence which constitutes less than 100%, but at least 20%, preferably at least 30%, more preferably at least 80% or even more preferably at least 90%, 95%, 98% or 99% of said polypeptide.

The fragment may also include a "biologically active fragment" which retains the biological activity of a given polypeptide or peptide. For example, a biologically active fragment of IL-12 or a biologically active fragment of one or more pathogen derived protein(s). The biologically active fragment constitutes at least greater than 1% of the biological activity of the entire polypeptide or peptide, preferably at least greater than 10% biological activity, more preferably at least greater than 25% biological activity and even more preferably at least greater than 50%, 60%, 70%, 80%, 90%, 95%, 98% and even 99% biological activity.

As generally used herein, a "homolog" shares a definable nucleotide or amino acid sequence relationship with a nucleic acid or polypeptide as the case may be. Included within the scope of homologs are "orthologs", which are functionally-related polypeptides and their encoding nucleic acids, isolated from other organisms. For example, homologs of mouse and human IL-12.

Nucleic Acids

The term "nucleic acid" as used herein designates single or double stranded mRNA, RNA, cRNA and DNA, said DNA inclusive of cDNA and genomic DNA. Nucleic acid includes primers, probes and oligonucleotides, such as oligodexoynucleotides (ODN). A nucleic acid may be native or recombinant and may comprise one or more artificial nucleotides, e.g. nucleotides not normally found in nature. Nucleic acid encompasses modified purines (for example, inosine, methylinosine and methyladenosine) and modified pyrimidines (thiouridine and methylcytosine).

Nucleic acid includes CpG nucleic acids. CpG nucleic acids include any suitable CpG nucleic acid, for example, CpG motif-containing oligodeoxynucleotide immunostimulatory sequences: (1) uniformly modified phosphorothioate (PS) oligodeoxyribonucleotides (ODNs), which appear to initiate B cell functions, but poorly activate dendritic cells (DCs) to make interferon (IFN)-alpha, and (2) chimeric PS/phosphodiester (PO) ODNs containing runs of six contiguous guanosines, which induce very high levels of plasmacytoid DC (PDC)-derived IFN-alpha, but poorly stimulate B cells as described in Marshall et al, 2003, J Leukoc Biol 73 781. The CpG oligonucleotides described herein are merely examples of suitable CpG oligonucleotides and it will be appreciated that a person skilled in the art will be able to select other suitable CpG oligonucleotides having a similar or different nucleotide sequence, or fragments of same or similar CpG oligonucleotides and CpG oligonucleotides of different lengths and comprising any suitable combination of nature or unnatural nucleotide bases.

As described in WO 00/31540, the CpG dinucleotide may form a core motif common to immunostimulatory DNA (Krieg et al., 1995, Nature 374 546). However, it is also clear that flanking sequence can be important, in that CpG sequences flanked by a cytosine (C) or guanine (G) nucleotide are less immunostimulatory (Krieg et al., 1995, supra).

CpG sequences are relatively common in bacterial DNA, and are generally unmethylated. In contrast, CpG sequences occur less commonly in vertebrate DNA (about 25% of what would be expected based on random base utilization) and are generally methylated (Bird, 1987, Trends Genet. 3 342; Bird, 1993, Cold Spring Harbor Symp. Quant. Biol. 58 281). Thus, by virtue of the presence of unmethylated CpG sequences, bacterial DNA can be distinguished by the immune system as being non-self, whereas a CpG suppressed@ vertebrate sequences are treated as self. It should also be noted that unmethylated vertebrate CpG sequences tend to be flanked by C or G nucleotides, rendering them less immunostimulatory. Accordingly, the nucleotide sequence comprising CpG and the amount of methylation may be selected by a skilled person to appropriately stimulate an immune response in accordance with the invention.

An "expression vector" may be either a self-replicating extra-chromosomal vector such as a plasmid, or a vector that integrates into a host genome. Expression vectors are well known in the art and a suitable expression vector may be selected for expression in humans. Such an expression vector may be suitable of expressing IL-12 in an animal. An expression vector may also be used to express a pathogen protein(s).

By "operably linked" is meant that said regulatory nucleotide sequence(s) is/are positioned relative to the recombinant nucleic acid to initiate, regulate or otherwise control transcription. For example, IL-12 nucleic acid and/or a pathogen nucleic acid(s) may be operably linked to a regulatory nucleotide sequence(s).

Regulatory nucleotide sequences will generally be appropriate for the host cell used for expression. Numerous types of appropriate expression vectors and suitable regulatory sequences are known in the art for a variety of hosts, including eukaryotes such as humans.

Pharmaceutical Compositions, Immunotherapeutic Compositions and Vaccines

A pharmaceutical composition comprises actives that may be "immunogenic agents" capable of eliciting an immune response in an animal. An immunogenic agent may comprise an antigenic component.

It will be appreciated that an immunogenic agent in one embodiment when administered to a subject, such as a human, may reduce infection by a pathogen and/or may improve recovery from an infection by a pathogen. Accordingly, a pharmaceutical composition or an immunogenic agent may provide partial protection or recovery and need not provide complete protective immunity against a pathogen. Partial protection against a pathogen may be useful, for example, by reducing severity of infection or improving survival or recovery of the subject from an infection by a pathogen. Partial protection preferably prevents clinical diagnosis of malaria or symptoms of malaria, including prevention of death of the infected subject.

In addition to administration of the immunogenic agent, one or more other agents may be administered to treat or prevent the infection or other ailment. For example, a pharmaceutical composition for preventing or treating malaria may be administered to a same subject as the immunogenic agent. This may be preferred in a situation where the immunogenic agent provides partial protection against *Plasmodium* spp infection and the disease malaria. In one embodiment, an anti-malaria pharmaceutical, such as chloroquine, atovaquone and/or proguanil is administered to a same subject being administered the immunogenic agent. In one embodiment, an anti-malaria pharmaceutical composition may be administered to improve protection and/or recovery from infection by a range of unknown *Plasmodium* spp or unknown strains. The anti-malaria pharmaceutical may be administered before, concurrently and/or after administration of the pharmaceutical composition of the invention.

A "vaccine" is capable of providing protective immunity against an organism. The vaccine may provide protection against a same (i.e. homologous) or different (i.e. heterologous) strain of an organism. The vaccine of the invention preferably is capable of providing protection against homologous and heterologous species, variants or strains. In a preferred embodiment, the vaccine is capable of protecting or treating a human from infection from one or more heterologous strains of *Plasmodium*, for example, one, two, three, four, fix, six, seven, eight, nine, ten, 100, 200, 300, 400, 500, 600, 700, 800, 900, 1000 and even more than 1000 different strains of *Plasmodium*. Preferably, the *Plasmodium* spp is selected from a species capable of infecting a human, for example *Plasmodium falciparum, Plasmodium vivax, Plasmodium malariae* and *Plasmodium ovale*. The vaccine is preferably capable of protecting or treating a human from one or more different strains of one or more different species of *Plasmodium*.

Immunogenic agents used as actives in a pharmaceutical composition may be suitable for immuno-therapy or vaccination of humans. An immunogenic agent when administered to an animal, for example a human, is capable of eliciting an immune response in said animal against the immunogenic agent.

A pharmaceutical composition includes an immunotherapeutic composition. An immunotherapeutic composition includes a vaccine.

Suitably, the pharmaceutical composition comprises a pharmaceutically-acceptable carrier. By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Any suitable route of administration may be employed for providing a patient with the pharmaceutical composition of the invention. For example, oral, rectal, parenteral, sublingual, buccal, intravenous, intraarticular, intramuscular, intradermal, subcutaneous, inhalational, intraocular, intraperitoneal, intracerebroventricular, transdermal and the like may be employed. Intramuscular and subcutaneous injection is appropriate for administration of immunogenic agents of the present invention.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for administration may be presented as discrete units such as vials, sachets, syringes and the like, each containing a pre-determined amount of one or more immunogenic agent, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be used as a therapeutic or prophylactic composition comprising a protein and/or nucleic acid of a pathogen, preferably a plurality of pathogen proteins, more preferably a majority of pathogen proteins, even more preferably an extract derived from the pathogen. In one embodiment, the vaccine comprises an immunogenic agent as described above. Preferably, the vaccine prevents or treats infection by a parasite, more preferably infection by one or more different species of *Plasmodium* spp or one or more strains thereof. Accordingly, in a preferred form, the vaccine protects against both homologous and heterologous strains of *Plasmodium* spp, preferably one or more different strains of one or more different species capable of infecting humans, in particular, a *Plasmodium* spp selected from the group consisting of: *Plasmodium falciparum, Plasmodium vivax, Plasmodium malariae* and *Plasmodium ovale.*

Accordingly, the invention extends to the production of vaccines comprising as actives an antigenic component of the invention. Any suitable procedure is contemplated for producing such vaccines. Exemplary procedures include, for example, those described in NEW GENERATION VACCINES (1997, Levine et al., Marcel Dekker, Inc. New York, Basel Hong Kong) which is incorporated herein by reference.

An immunogenic agent according to the invention can be mixed, conjugated or fused with other antigens, including B and/or T cell epitopes of other antigens. In addition, it can be conjugated to a carrier as described below.

When a haptenic peptide is used (i.e., a peptide which reacts with cognate antibodies, but cannot itself elicit an immune response), it can be conjugated with an immunogenic carrier. Useful carriers are well known in the art and include for example: thyroglobulin; albumins such as human serum albumin; toxins, toxoids or any mutant cross reactive material (CRM) is of the toxin from tetanus, diptheria, pertussis, *Pseudomonas, E. coil, Staphylococcus,* and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic polypeptide may be used. For example, a haptenic peptide can be coupled to a T cell epitope of a bacterial toxin, toxoid or CRM. In this regard, reference may be made to U.S. Pat. No 5,785,973 which is incorporated herein by reference.

The vaccines can also contain a physiologically-acceptable carrier, diluent or excipient such as water, phosphate buffered saline or saline.

The vaccines and immunogenic agents may include an adjuvant as is well known in the art. Suitable adjuvants include, but are not limited to adjuvants for use in human for example: aluminum hydroxide (alum), IL-12, CpG-ODN, SBAS2, SBAS4, QS21, or ISCOMs. Preferably, the adjuvant is alum.

Immunotherapeutic Agent and Vaccine Development
Heterologous Antigens

Malaria is a disease characterized by several species and strains of pathogenic organisms, i.e. *Plasmodium* spp as described herein. Accordingly, malaria is used as an example of a suitable disease that may be controlled by reducing severity of infection and improving recovery, or preventing and/or treating by the pharmaceutical composition of the present invention. In relation to preparation of a malaria immunotherapeutic agent and vaccine, an antigenic component derived from whole *Plasmodium* spp, for example *P. falciparum,* or extract thereof, would comprise every parasite antigen, thus minimizing the consequences of limited immunological recognition of any one antigen and the consequences of antigenic polymorphisms. Further, the antigenic component may comprise antigens derived from one or more different species of *Plasmodium,* including for example a combination of two or more different species of *Plasmodium* spp or a combination of two or more different strains of one or more different species of *Plasmodium.* For example, the antigenic component may comprise one or more antigens derived or obtained from one or more *Plasmodium* spp selected from the group consisting of: *P. falciparum, P. vivax, P. malariae, P. ovale, P. knowlesi, P. berghei, P. yoelii, P. chabaudi* and *P. vinckei.* In a preferred form, the one or more *Plasmodium* spp is selected from those capable of infecting human, including those selected from the group consisting of: *P. falciparum, P. vivax, P. malariae, P. ovale,*

Not being bound by theory, a combination of a very low dose of antigenic component together with an IL-12 inducing adjuvant such as CpG is thought to lead to a potent T cell response (cell mediated immunity; CMI). Such responses are not induced by natural infection, possibly because of apoptosis of parasite-specific T cells at high parasite density. Consequently, the antigens that might have been recognized by T cells are not under immune pressure and are likely to be conserved (Makobongo et al., 2003). Inducing such CMI using a pharmaceutical composition of the present invention may result in immunity against one or more *Plasmodium* spp or one or more strains of *Plasmodium* spp, preferably a plurality of *Plasmodium* strains, more preferably all *Plasmodium* strains. For example, one, two, three, four, five, six, seven, eight, nine, ten or more strains of a *Plasmodium* spp. A skilled person would be aware of *Plasmodium* strains, in particular those strains capable of infecting humans and causing malaria. As new and unknown strains may cause malaria, including different strains in different regions of the world, the present invention in a preferred form is particularly useful in being capable of reducing infection or improving recovery from infection by one or more strains of *Plasmodium* spp. In a preferred embodiment, administration of the pharmaceutical composition results in immunity against one or more *Plasmodium* spp, preferably a plurality of species, more preferably all *Plasmodium* spp. For example, one, two, three, four, five, six, seven, eight or more species. In a preferred form of the invention, the *Plasmodium* spp is selected from the group consisting of: *P. falciparum, P. vivax, P. malariae, P. ovale, P. knowlesi, P. berghei, P. yoelii, P. chabaudi* and *P. vinckei*. In a more preferred form, the one or more *Plasmodium* spp is selected from those capable of infecting human, including those selected from the group consisting of: *P. falciparum, P. vivax, P. malariae* and *P. ovale*, While it is presently less practical to develop a low dose live (including attenuated) pathogen pharmaceutical composition for widespread human use, a low dose of a "dead" or killed pathogen or extract therefrom as described herein could be practically administered and widely distributed. Not being bound by theory, it will be appreciated that an extract from killed whole organism may present pathogen antigens differently to immune cells, e.g. T-cells, antigen presenting cells, B-cells, than live pathogen (including attenuated pathogen), which may provide an improved immune response or heterologous protection. Also, in a preferred embodiment, the pharmaceutical composition comprises CpG-oligonucleotides, which are inexpensive and have been safely administered in humans. Accordingly, a preferred form of an immunotherapeutic agent and vaccine comprises a low dose of an antigenic component comprising an inactivated *Plasmodium* spp in combination with CpG-oligonucleotide. Not being bound by theory, it will also be appreciated that in the preferred form comprising CpG-oligonucleotide, IL-12 will be produced by dendritic cells stimulated by binding CpG-oligonucleotide. IL-12 will activate T-cells within a localised area where an immune response is required and not systemically, as would be the case if IL-12 was injected into the animal. Accordingly, non-specific effects are minimised.

An estimate of the amount of parasite antigen required to stimulate an appropriate immune response may be approximated based on the example herein and also as about an equivalent amount of antigen present in naive volunteers described as above in Pombo et al, 2002, supra, eight days after being administered 30 parasites, i.e. about 1000-3000 parasites/ml blood equivalents. Using modern proteomics and protein chemistry it is entirely feasible to purify an antigenic component of *Plasmodium* spp from red cell antigens (primarily red cell membranes and hemoglobin). Any slight chance that potentially deleterious anti-red cell immune responses might result would be further greatly reduced by growing the *P. falciparum* parasites in O NEG (Auniversal donor@) blood.

It may also be feasible to recombinantly express a pool of pathogen proteins, for example *Plasmodium* spp proteins, that represent a majority of *Plasmodium* spp proteins. This may mimic an extract derived from *Plasmodium* spp by providing a broad range of antigens, which may be suitable for protecting against heterologous challenge.

The feasibility of the above approach rests with the extremely low dose of antigen required for protection and an ability of new adjuvants, such as CpG (already known to be efficacious in humans) to promote strong immune responses. If large doses of parasites ($10^7$-$10^9$ equivalents) were required, this approach would be far more commercially difficult and impractical due to logistic reasons; however, the examples herein provide evidence that not only can low dose immunization be effective, but it will be more effective than high dose.

Discussion

Complete protective immunity to malaria requires the immune system to be capable of recognising and eliminating different variants, strains and species of *Plasmodium*, each expressing a wide range of polymorphic antigens. The development of natural immunity to *P. falciparum* appears to rely predominantly on exposure a wide repertoire of different pathogens, eg parasite strains and variants, although a small component of non-strain-specific immunity may also be involved. To further complicate the development of natural immunity, the parasite induces immunosuppression and apoptosis of immune cells, which impairs immune responses, particularly to cryptic or poorly immunogenic eptiopes/antigens. When considering the development of a vaccine against malaria, imitating the mechanism of natural immunity is impractical and to a certain degree undesirable.

The apoptosis of immune cells and the suppression of proliferative T cell responses seen with a fulminant malaria infection did not occur when a single low dose infection of parasite was administered, and proliferative responses to both homologous and heterologous parasite antigen were maintained after three low dose infections. This would allow the development of a potentially novel immune response, possibly targeting conserved epitopes that could produce a strain- and variant-transcending immunity.

Challenge infections demonstrate that three low dose infections can induce protective immunity capable of controlling infection with a homologous parasite and with a heterologous parasite strain and variant. It is likely that immune responses are predominantly targeting conserved epitopes, and this is supported by flow cytometric analysis of PRBC stained with prechallenge sera from low dose mice and from mice given three full infections with live parasite (representative of a natural infection). Whilst full infections induce the production of antibodies that strongly recognise antigens on the surface of homolgous PRBC, low dose infections produced antibodies that only poorly recognised homologous PRBC.

An important aspect of vaccine development against infectious diseases, including malaria, is the identification of an appropriate adjuvant that is both capable of stimulating a protective immune response and safe for use in humans. Aluminum hydroxide (alum) is not always the most appropriate adjuvant given its potential to stimulate a Th2 type immune response characterized by IgG1 and IgE production and the lack of induction of cytotoxic T cell responses (5). This is particularly problematic in the development of vaccines against diseases caused by intracellular pathogens such as protozoan parasites, including intraerythrocytic *Plasmodium* parasites, the causative agent of malaria. Protective immunity against intracellular pathogens is generally dependent on Th1 type immune responses. However, protective immunity against blood-stage malaria is particularly complex and requires a concerted effort by a Th1 type cellular immune response and humoral immunity possibly involving a Th2 type response (24,29).

Co-adsorption of antigen and IL-12 to alum promotes both Type 1 cytokine and antibody responses (19,21). Since both cellular and humoral responses have been implicated in protective immunity to malaria, the inventors hypothesised that immunization with the combination of malaria antigen and IL-12 co-adsorbed to alum may enhance protective immunity to blood-stage malaria. To investigate this possibility, the inventors examined the feasibility of using crude malaria antigen co-adsorbed with IL-12 to alum as a vaccine against blood-stage malaria in the mouse model of P. chabaudi AS. Cellular and humoral immune responses were compared in A/J mice immunized with antigen plus IL-12 in alum as well as antigen alone, antigen in alum, or antigen plus IL-12 and boosted three weeks later with antigen alone prior to challenge infection.

A/J mice are susceptible to primary P. chabaudi AS infection and experience fulminant and lethal parasitemia by 10-13 days post-infection (36). During the first week of infection, spleen cells from these mice produce high levels of IL-4 and low levels of IFN-γ in vitro in response to parasite antigen (38). Determination of proliferation and cytokine production in vitro by spleen cells from A/J mice immunized with the various vaccine combinations revealed that spleen cells from mice immunized with malaria antigen plus IL-12 in alum had the highest levels of proliferation as well as of IFN-γ production in response to specific antigen. Spleen cells from these mice also produced lower levels of the Th2 cytokine IL-4 as well as the Th1 cytokine, TNF-γ and low levels of IL-10.

The present results indicate that vaccination with the combination of malaria antigen plus IL-12 co-adsorbed to alum induced a Th1 immune response in vaccinated mice. The induction of a Th1 immune response by administration of malaria antigen plus IL-12 co-adsorbed to alum is relevant given the important role of Type 1 cell-mediated and humoral immune responses in mediating naturally-induced immunity against blood-stage malaria in mice infected with blood-stage P. chabaudi AS, and possibly humans (24,29,39,40).

Importantly, immunization with the combination of malaria antigen plus IL-12 in alum induced strong protective immunity against challenge infection with blood-stage P. chabaudi AS in both susceptible A/J and resistant C57BL/6 mice. In contrast to control A/J mice which experience a severe course of parasitemia and 100% mortality (36), immunization with either antigen plus IL-12 or antigen plus IL-12 co-adsorbed to alum resulted in less severe courses of infection and significant decreases in peak parasitemia level. However, only mice immunized with antigen plus IL-12 in alum experienced 100% survival. Moreover, the protection induced by this formulation was long-lasting since mice challenged 3 months after boosting were still completely protected against P. chabaudi AS. This group of animals had significant decreases in peak parasitemia levels and time to parasite clearance comparable to mice challenged 2 weeks after boosting. In both instances, there was 100% survival of vaccinated mice.

Although CD4$^+$ T cells are known to play an important role in immunity to primary blood-stage P. chabaudi AS (24,29), little is known about the role of these cells in vaccine-induced immunity to blood-stage malaria. Earlier studies by Langhorne and colleagues (25) demonstrated that depletion of CD4$^+$ T cells from immune C57BL/6 mice results in a low, transient parasitemia following challenge with P. chabaudi AS which is eventually cleared. In contrast, the present results in CD4$^+$ T cell depleted, immunized mice indicate that CD4+ T cells play a critical role in immunity induced by vaccination with malaria antigen and IL-12 in alum. The inventors observed that immunized CD4$^+$ T cell depleted mice experienced severe and lethal infections when challenged with P. chabaudi AS.

It is likely that CD4$^+$ T cells participate in immunity induced by immunization with malaria antigen and IL-12 co-adsorbed to alum by producing IFN-γ. NK cells may be a source of IFN-γ in mice immunized with malaria antigen and IL-12 in alum. NK cells have been found to produce IFN-γ early in infection with various species of mouse malaria parasites, including P. chabaudi AS (9,28). Recent studies in humans demonstrated that P. falciparum infected red blood cells induce IFN-γ production by NK cells from individuals infected with P. falciparum and non-exposed donors (3). IFN-γ is considered to be a major component of innate and acquired immunity to primary blood-stage P. chabaudi infections (11,24,40,42). The inability to protect GKO compared to wildtype C57BL/6 mice against challenge infection as shown here indicates that IFN-γ is also a critical cytokine in vaccine-induced immunity following immunization with malaria antigen and IL-12 co-adsorbed to alum. In humans, IFN-γ production has been found to correlate with resistance to reinfection with Plasmodium falciparum as well as with protection from clinical attacks of malaria (6,8,26). Based on these observations, it has been concluded that IFN-γ production should be considered as an important hallmark of effector T cell function for development of an effective malaria vaccine (14,32). Our results in the present report support this contention.

During primary P. chabaudi AS infection, mice rendered B cell deficient by treatment from birth with anti-IgM antibodies or μ-MT mice with targeted disruption of the membrane exon of the immunoglobin μ-chain gene can control acute parasitemias similar to intact mice (41,44). However, B cell-deficient mice maintain a chronic low level of parasitemia indicating that effective parasite clearance at the later, chronic stage of infection requires the presence of B cells. (41,44). In addition to their ability to produce antibody, B cells may also play a role via production of IL-10 (41) in the switch from Th1 cells producing IFN-γ, which mediates control of acute parasitemia, to Th2 cells which provide help for antibody production leading to clearance of primary blood-stage P. chabaudi AS infection. Studies in μ-MT mice also showed that B cell-deficient animals are unable to control a challenge infection and develop parasitemia levels similar in magnitude to a primary infection (44). These findings suggest that B cell-dependent mechanisms may be important for an effective memory response to P. chabaudi AS infection (44). In the present study, we observed that immunization of B cell-deficient μ-MT mice with malaria antigen and IL-12 co-adsorbed to alum is ineffective in providing enhanced protection against challenge infection with P. chabaudi AS suggesting a role for a B cell-dependent mechanism(s) in vaccine induced immunity.

The investigators also examined the possibility of replacing IL-12 with immunostimulatory CpG-ODN. Because of its ability to induce a Type 1 pattern of cytokine production dominated by IL-12 and IFN-γ with little secretion of Type 2 cytokines, CpG-ODN have been found to be useful as adjuvants for vaccines, including peptide vaccines, against a variety of pathogens (4,5,7,15,23,30,35,45). Near and colleagues (30) recently demonstrated that vaccination with the combination of CpG-ODN and a defined single P. yoelii antigen, MSP1$_{19}$, in alum resulted in a dramatic elevation in IFN-γ production as well as elevated production of IL-10 by MSP1$_{19}$-stimulated splenocytes suggesting induction of a mixed Th1/Th2 response. In mice vaccinated with this formulation, IgG1 was found to be the predominant antibody isotype in sera although increased levels of MSP1$_{19}$-specific IgG2a, IgG2b, and IgG3 isotype antibodies were also observed. Furthermore, increased antibody levels were found to correlate with protection against challenge infection with a high dose of *P. yoelii* PRBC. The present experimental results demonstrate that inclusion of immunostimulatory CpG-ODN instead of IL-12 in the vaccine formulation provides strong protection against blood-stage *P. chabaudi* AS infection in A/J mice. Also, immunization with CpG-ODN and crude malaria antigen in alum induces high levels of malaria-specific IgG2a in A/J mice before challenge infection in comparison to immunization with control ODN and antigen in alum (data not shown).

Murine models are commonly used to study host parasite interactions and mechanisms of immunity to malaria in humans and the murine model often closely predicts the outcome in humans as discussed in Doolan and Hoffman, 2000, J. Immunol. 165 1453, incorporated herein by reference. For example, it is well known that in the murine *P. Ch. Chabaudi* model, parasites undergo recrudescence. An immune response to *P. Ch. Chabaudi* is the most well characterized model. Parasitaemia in this mouse model most closely resembles *P. faiciparum* in humans, which is the most important type of malaria in humans.

In conclusion, it is possible to enhance the potency of a crude malaria antigen in alum vaccine formulation by inclusion of agents with immunostimulatory properties, such as IL-12 or CpG-ODN. Immunity induced by immunization with malaria antigen and IL-12 co-adsorbed to alum induced a long-lasting, Th1 immune response required for protection against challenge infection with *P. chabaudi* AS infection.

In order that the invention may be readily understood and put into practical effect, particular preferred embodiments will now be described by way of the following non-limiting examples.

EXAMPLE 1

Vaccination Against Blood-Stage Malaria Using Th1 Immunostimulatory Adjuvants
Materials and Methods
Mice Age- and sex-matched mice, 6-8 wk old, were used in all experiments. A/J mice were purchased from The Jackson Laboratory (Bar Harbor, Me.) and C57BL/6 mice from Charles River Laboratories (St. Constant, Quebec). Interferon-γ knockout (GKO) mice on the C57BL/6 background were bred in the animal facility of the Montreal General Hospital Research Institute from breeding pairs of GKO mice, which were originally from Genentech, Inc. (South San Francisco, Calif.) and backcrossed onto the C57BL/6 strain for eight generations, by Dr. F. P. Heinzel (Case Western Reserve University School of Medicine, Cleveland, Ohio) (16). B cell-deficient μ-MT with targeted disruption of the membrane exon of the immunoglobin μ-chain gene or B cell knockout (BKO) mice were originally derived on a 129 X C57BL/6 background and backcrossed to the C57BL/10 background for 12 generations (20,22). B cell-deficient μ-MT and wild type C57BL/10SgSnAi mice were obtained from Taconic Farms, Inc. (Germantown, N.Y.).
CD4+ T Cell Depletion Monoclonal anti-CD4 antibody from the hybridoma clone GK1.5 was raised as ascites fluid in BALB/c mice as previously described (33) and incorporated herein by reference. The ascites fluid was delipified, dialyzed, and quantitated for concentration of rat IgG. Mice were treated with the first dose of 500 μg anti-CD4 antibody intraperitoneally (i.p.) 3 days prior to infection. Following infection, 200 μg was administered i.p. 3 times per week until the end of the experiment. Control mice received purified rat IgG at similar dosages and timing. Treatment with GK1.5 monoclonal antibody consistently depletes >98% of CD4+ T cells based on fluorocytometric analysis (33,37) and functional studies (33).
*P. chabaudi* AS Infection and Antigen Preparation

*P. chabaudi* AS was maintained as previously described (33). Naive and immunized mice were infected i.p. with 1×10$^6$ PRBC. The course and outcome of infection were monitored by previously described procedures (33). For determination of cytokine and antibody levels in sera, mice were sacrificed at the indicated times and blood was obtained by cardiac puncture, allowed to clot for 30 min at 4° C., and centrifuged at 3,000×g for 3 min. Sera were collected and stored at 4° C. for measurement of IL-12 p70 or at −20° C. for determination of the levels of other cytokines and malaria-specific antibodies.

Antigen was prepared by modification of a freeze-thaw protocol described by Amante and Good (2). Briefly, blood from A/J mice with parasitemias of 40-45% was collected, pooled and centrifuged at 300×g for 10 minutes. The red blood cell pellet was subjected to 2 rounds of lysis with distilled H$_2$O and centrifugation at 10,000×g for 25 minutes. After 2 washes with PBS, the parasite pellet was resuspended in PBS and subjected to 3 cycles of freeze-thaw at −70° C. and 37° C. The suspension, containing both soluble and particulate antigens, was further disrupted by passage 2-3 times through a syringe with a 25 g needle.
Immunization Protocol Malaria antigen equivalent to 1-1.5×10$^7$ PRBC was mixed with 1 μg of mrIL-12 (a kind gift from Wyeth, Genetics Institute Cambridge, Mass.) to a volume of 50 μl with PBS. An equal volume of alum (Imject® Alum, Pierce Chemical Co, Rockford, Ill.) was added and the suspension was mixed thoroughly. Mice were immunized with 0.1 ml subcutaneously (s.c.) on the nape. Other groups of mice were also immunized in a similar manner with the following vaccine combinations: antigen suspended in PBS, antigen admixed in alum, and antigen admixed with 1 μg of mrIL-12 in PBS. Three weeks later, the antigen treated groups were boosted with the same amount of antigen in 0.1 ml PBS injected i.p. Mice were challenged i.p. with 1×10$^6$ PRBC two weeks later.
CpG DNA Oligodeoxynucleotids (ODN) comprising CpG motifs (CpG-ODN No. 1826) and control ODN (No. 1982) were provided by Coley Pharmaceuticals Canada (Ottawa, ON, Canada). 100 μg of CpG-ODN or control ODN was admixed with antigen and alum and used according to the standard immunization protocol described above.

The nucleotide sequences of CpG nucleic acids used herein are as follows:

```
ODN No. 1826 = TCCATGACGTTCCTGAGTT;   (SEQ ID NO: 4)

ODN No. 1982 = TCCAGGACTTCTCTCAGGTT  (SEQ ID NO: 3)
```

Spleen Cell Culture and Proliferation Assay

Spleens from immunized mice were removed aseptically and pressed through a sterile fine wire mesh with 10 ml RPMI 1640 (Gibco-Invitrogen, Burlington, ON, Canada) supplemented with 5% heat-inactivated FCS (Hyclone Laboratories, Logan, UT), 25 mM HEPES (Gibco-Invitrogen), 0.12% gentamicin (Schering, Montreal, QC, Canada), and 2 mM glutamine (Gibco-Invitrogen). Cell suspensions were centrifuged at 350×g for 10 minutes. Red blood cells were lysed with 0.175 M $NH_4Cl$ and the cells were washed twice in fresh medium. Membrane debris was removed by filtering the cell suspensions through sterile gauze. The viability of the cells was determined by trypan blue exclusion and was always >90%. Total cell counts were performed on individual samples. For proliferation assays, spleen cells were adjusted to $2.5×10^6$ cells/ml and aliquots of 0.1 ml were plated in triplicate in 96-well flat-bottom plates, stimulated with $1×10^6$ washed PRBC/ml as malaria parasite antigen or medium as control and incubated for 72 h at 37° C. in a humidified $CO_2$ incubator. During the last 16 h of culture, 1 μCi of $^3H$-thymidine (specific activity, 6.7 Ci/mmol) was added to each well, the cells were harvested with an automatic cell harvester, and the incorporated radioactivity was measured in a liquid scintillation counter. For determination of cytokine production, spleen cells were adjusted to $5×10^6$ cells/ml and aliquots of 1 ml were plated in triplicate in 24-well tissue culture plates in the presence or absence of $1×10^6$ PRBC, as described above, and incubated for 48 h at 37° C. in a humidified $CO_2$ incubator. Supernatants were collected, centrifuged at 350×g for 5 min, and stored at 4° C. or at −20° C. until assayed for cytokine levels.

Cytokine ELISAs

Cytokine levels in sera and spleen cell supernatants were measured using two-site sandwich ELISAs for IFN-γ and TNF-α as previously described (34,37). For IL-4, the capturing and detecting antibodies were BVD4-1D11 mAb and biotinylated BVD6-24G2 mAb, respectively. For IL-10, JES5.2A5 mAb (American Type Culture Collection, Rockville, Md.) and biotinylated SXC-1 mAb (BD Bioscience, Mississauga, ON) were used as capturing and detecting antibodies, respectively. Standard curves for each cytokine were generated using recombinant cytokines (BD Bioscience, Mississauga, ON). Reactivity was revealed using ABTS substrate (Roche, Laval, QC) and OD values were read in a microplate reader at 405 nm with a reference wavelength of 492 nm.

Malaria-Specific Antibody ELISA

Serum levels of *P. chabaudi* AS specific antibody isotypes were determined by ELISA. *P. chabaudi* AS antigen was prepared as described previously (49). Immulon II plates (Dynatech, Chantilly, Va.) were coated with parasite antigen at a concentration of approximately 4-5 μg/ml in PBS based on OD at 280 nm overnight at 4° C. and subsequently blocked with 1% BSA in PBS for 1 h. Individual serum samples were serially diluted 2-fold and 50 μl of each dilution were added to the plate and incubated for 2 h at room temperature. Data shown are based on values obtained at the following dilutions: total Ig, 1:20, IgG1, 1:10, and IgG2a, 1:10. After extensive washing, horseradish peroxidase-conjugated goat anti-mouse isotype antibodies (SBA, Birmingham, Ala.) were added and incubated at room temperature for another 2 h. Reactivity was visualized using ABTS substrate and OD values were read in a microplate reader at 405 nm with a reference wavelength of 492 nm. Antibody levels in serum are expressed as relative OD.

Statistical Analysis

Data are presented as mean±SEM. Statistical significance of differences in means between experimental and control groups was analyzed by Student's t-test using SAS/STAT software (SAS Institute, Cary, N.C.). A $p<0.05$ was considered significant.

EXAMPLE 2

Immunization with Malaria Antigen Plus IL-12 in Alum Induces a Th1 Immune Response.

Since a strong Th1 immune response is associated with protective immunity to acute blood-stage *P. chabaudi* AS during a primary infection, the type of immune response induced by inclusion of IL-12 in a vaccine formulation was first evaluated. *P. chabaudi* AS susceptible A/J mice were immunized s.c. with a freeze-thaw preparation of blood-stage malaria antigen alone, antigen in alum, antigen plus IL-12, or antigen plus IL-12 in alum and boosted three weeks later by i.p. injection with antigen alone. Two weeks later, prior to challenge infection, immunized mice and untreated, control A/J were sacrificed and proliferation and cytokine production by spleen cells were analyzed in vitro. As shown in Table 1, immunization with either antigen in alum or the combination of antigen plus IL-12 in alum resulted in significantly increased antigen-specific proliferation compared to the response of control A/J mice (p=0.02 and p=0.037, respectively). However, the combination of antigen plus IL-12 in alum resulted in greater than a 2-fold increase in proliferation compared to antigen in alum, which represents a significant difference between the two groups. Furthermore, in comparison with spleen cells from mice immunized with antigen in alum, spleen cells from mice immunized with the combination of antigen plus IL-12 in alum produced significantly higher levels of the Th1 cytokines, IFN-γ and TNF-γ, and significantly lower levels of IL-4. Spleen cells from mice immunized with the combination of antigen plus IL-12 in alum also produced modest levels of IL-10, which were significantly higher than the response of cells from mice immunized with antigen in alum.

The levels of total malaria-specific antibody and IgG1 and IgG2a in the sera of immunized A/J mice were also analyzed two weeks after boosting prior to challenge infection. Total malaria-specific antibody was significantly and similarly increased in the three groups of immunized animals compared with the levels of total specific antibody in mice immunized with antigen alone (FIG. 1A). Malaria specific IgG1 was significantly increased in the groups immunized with antigen in alum and the combination of antigen plus IL-12 in alum compared to IgG1 levels in mice immunized with antigen alone (FIG. 1B). However, the level of malaria-specific IgG1 was significantly higher in the group immunized with antigen in alum compared to those immunized with the combination of antigen plus IL-12 in alum. The levels of specific IgG2a were significantly increased compared to controls only in mice immunized with the combination of antigen plus IL-12 in alum (FIG. 1C). These findings demonstrate that immunization with the combination of malaria antigen plus IL-12 in alum induced high levels of production of the Th1 cytokine IFN-γ and parasite-specific IgG2a. In addition, mice immunized with this combination produced significantly lower levels of antigen-specific IL-4 and IgG1 compared to mice immunized with antigen in alum in the absence of IL-12.

EXAMPLE 3

Immunization with Malaria Antigen Plus IL-12 in Alum Induces Protection Against Challenge Infection with Blood-stage *P. chabaudi* AS.

To compare the efficacy of vaccination with the various combinations in conferring protective immunity, groups of A/J mice, immunized as described above, were challenged i.p. with *P. chabaudi* AS two weeks after boosting and the course of parasitemia and the outcome of infection were followed. Similar to control mice, mice immunized with antigen alone or antigen in alum suffered a severe course of parasitemia with high peak parasitemia levels and high mortality (FIG. 2A and 2C). Mice immunized with antigen plus IL-12 or antigen plus IL-12 in alum experienced less severe courses of infection with significantly lower peak parasitemia levels compared to control mice (p<0.001 and p<0.001, respectively; FIG. 2B). In the case of mice immunized with antigen plus IL-12 in alum, there was a delay of 1-2 days in peak parasitemia level compared to unimmunized mice. Although antigen plus IL-12 was effective in significantly reducing peak parasitemia compared to control mice, only 60% (9/15) of mice immunized with this combination survived while 100% (25/25) of mice immunized with the combination of antigen plus IL-12 in alum survived challenge infection with *P. chabaudi* AS. These results indicate that antigen plus IL-12 in alum was the best combination for conferring protection against blood-stage malaria in terms of reduced parasitemia and enhanced survival.

EXAMPLE 4

Immunization with Malaria Antigen Plus IL-12 in Alum Induces Long-Lasting Protection An important characteristic of an effective malaria vaccine is that the elicited immunity is long-lasting. To address this issue, A/J mice were immunized with the combination of antigen plus IL-12 in alum and challenged as before, that is, 2 weeks after boosting, or 12 weeks after boosting. Similar to mice challenged 2 weeks after boosting, A/J mice challenged at 12 weeks were solidly immune (Table 2). Long-lasting protection induced in these animals by malaria antigen plus IL-12 in alum was evident by a number of parameters. Importantly, there was a significant decrease in peak parasitemia compared to unimmunized A/J mice (p<0.001). In addition, the number of days required to clear parasites from the blood of mice challenged 12 weeks after boosting was similar to mice challenged 2 weeks after boosting and there was 100% survival among all immunized mice regardless of the time of challenge infection.

EXAMPLE 5

Protective Immunity Induced by Immunization with Malaria Antigen Plus IL-12 in Alum Requires CD4$^+$ T Cells and IFN-$\gamma$.

To investigate the mechanism of protective immunity induced by vaccination with the combination of antigen plus IL-12 in alum, immunized A/J mice were depleted of CD4$^+$ T cells by treatment with GK1.5 mAb 3 days prior to and three times per week during the challenge infection with *P. chabaudi* AS. Parasitemia and survival were monitored for 4 weeks post challenge infection. Consistent with the results shown above, intact immunized A/J mice suffered a mild course of infection and survived challenge infection. In contrast, CD4$^+$ T cell depleted mice experienced fulminant infections with significantly higher peak parasitemia levels than rat IgG treated mice (p=0.008) (FIG. 3A) and the animals died by day 11 post challenge.

To determine the role of IFN-$\gamma$ in vaccine-induced protection, GKO mice on the resistant C57BL/6 background and wildtype C57BL/6 mice (36) were immunized with antigen plus IL-12 in alum. Immunized as well as untreated, control GKO and wildtype mice were challenged with *P. chabaudi* AS as described above. The course of parasitemia and outcome of infection were followed for 4 weeks in control and immunized mice of both genotypes (FIG. 3B and 3C). As we have shown previously, control GKO mice developed significantly higher levels of peak parasitemia on day 7 compared to their wildtype counterparts (64.2±3.35 vs. 38.7±4.43, respectively; p<0.0001). Furthermore, immunized wildtype C57BL/6 mice had a significantly lower peak parasitemia level which occurred one day later compared to wildtype mice without immunization (p<0.0001; FIG. 3B) indicating that immunization with antigen plus IL-12 in alum induced protection in resistant C57BL/6 as well as susceptible A/J hosts. In contrast to increased protection, as defined by the level of peak parasitemia, observed in wildtype mice, there was no significant difference in peak parasitemia levels in immunized versus untreated GKO mice (55.31±1.37 vs. 64.2±3.35, respectively; p=0.05). The timing of the peak parasitemia was delayed from day 7 to day 9 in immunized compared to control GKO mice. However, 100% of GKO mice, whether immunized or not, succumbed to challenge infection by day 12 (data not shown and 40). Taken together, these results demonstrate the crucial roles of CD4+ T cells and IFN-$\gamma$ in the development of protective immunity against blood-stage malaria induced by immunization with *P. chabaudi* AS antigen plus IL-12 co-adsorbed to alum.

EXAMPLE 6

Protective Immunity Induced by Immunization with Malaria Antigen Plus IL-12 in Alum Requires B Cells.

As shown above, immunization of A/J mice with malaria antigen plus IL-12 in alum induced high levels of total malaria-specific antibody, IgG2a, and IgG1, and conferred the highest level of protection against challenge infection with blood-stage *P. chabaudi* AS. These observations suggested to us that the B cell response is an integral component of the mechanism of protective immunity induced by immunization with the lo combination of malaria antigen and IL-12 co-adsorbed to alum. The role of B cells in protective immunity induced by vaccination with antigen plus IL-12 in alum was further investigated using B cell-deficient μ-MT mice on the resistant C57BL/10 background (36). As previously observed (41,43,44), unimmunized male (FIG. 4A) and female (FIG. 4C) B cell-deficient mice compared to intact C57BL/10 mice (FIG. 4B and 4D) experienced recurrent bouts of recrudescent parasitemia until the experiment was terminated 90 days after challenge infection. Following immunization, peak parasitemia levels in male and female intact C57BL/10 mice were significantly decreased (p<0.001 for male mice and p<0.05 for female mice). Challenge infection was cleared in both male and female immunized C57BL/10 mice although female mice experienced several recrudescent parasitemias between 5 and 10%. Despite immunization, male and female B cell-deficient mice experienced peak parasitemias which were not significantly reduced compared to unimmunized, B cell-deficient mice. Although immunized B cell-deficient mice suffered fewer and significantly lower recrudescent parasitemias compared to their unimmunized counterparts, they were unable to clear the infection completely and low levels of parasitemia (1-5%) persisted throughout the chronic stage of infection until the experiment was terminated on day 90.

EXAMPLE 7

CpG-ODN Can Replace IL-12 as an Adjuvant for Immunization Against Blood-Stage Malaria It is possible that other agents, such as CpG-ODN, with potent immunostimulatory properties could also be useful as an adjuvant in a vaccine against blood-stage malaria. CpG-ODN has been shown to induce production of IL-12 which, in turn, enhances IFN-$\gamma$ production, antibody production by B cells, and cytotoxicity of NK cells and CD8$^+$ T cells (4,5,7, 15,23). To determine if CpG-ODN can replace IL-12 as an adjuvant in the blood-stage malaria vaccine, A/J mice were immunized with malaria antigen plus 100 µg CpG-ODN or control-ODN in alum, using the standard protocol, and challenged with P. chabaudi AS. As shown in FIG. 5, CpG-ODN was as effective as IL-12 in inducing protection against challenge infection with P. chabaudi AS. Mice immunized with malaria antigen plus CpG-ODN in alum had a course of parasitemia and 100% survival following challenge infection with P. chabaudi AS similar to mice immunized with antigen plus IL-12 in alum. There was a significant decrease in peak parasitemia level in mice immunized with antigen plus CpG-ODN in alum compared to mice immunized with antigen plus control ODN in alum ($p<0.001$) and mice in the former group cleared the parasite by 2 weeks post infection. The combination of antigen plus control ODN in alum was not protective and 100% of the mice in this group succumbed to challenge infection with fulminant parasitemia levels by day 10 post infection.

EXAMPLE 8

Low Dose of Whole Pathogen and Heterologous Challenge
Materials and Methods
Mice Female C57Bl/6j mice, 8-12 weeks old, were obtained from the Animal Resources Centre (Willeton, WA, Aust.). Mice were housed under specific pathogen-free conditions. All experiments were approved by the Bancroft Research Centre Ethics Committee.
Parasites Recently mosquito-passaged stabilates of P. c. chabaudi AS and P. c. chabaudi CB were supplied by Richard Carter, Institute of Cell, Animal and Population Biology, University of Edinburgh, UK. Parasites were cryopreserved in glycerolyte 57 (Baxter Healthcare Corporation, Deerfield, Ill., USA). To infect mice with a specific dose of parasite, blood was collected from the tail vein of an infected animal into phosphate buffered saline, adjusted to the appropriate concentration of PRBC and injected immediately into recipient mice. Parasitaemias were monitored by Giemsa-stained thin tail blood smears and recorded as the percentage of PRBC.
Anti-malarial Treatment A single tablet of the anti-malarial drug Malarone (250 mg atovaquone, 100 mg proguanil hydrochloride) (Glaxo-Wellcome Australia Ltd, Boronia, Vic, Aust.) was allowed to dissolve in 125 mL distilled water. To completely cure P.c.chabaudi AS infection in mice, 100 uL of this solution (0.2 mg atovaquone, 0.08 mg proguanil) was administered by oral gavage daily for 4 consecutive days.
Collection of Primary or Recrudescent Variants of P.c.chabaudi AS Frozen PRBC, which had been passaged through mice no more than 3-4 times following mosquito passage and so consisted largely of the primary variant, were thawed and used to infect one or two passage mice. The primary variant was collected from these mice by arterial tail bleed at the time of the first parasitaemia peak (6-12 days post-infection), and stored in Glycerolyte 57 at $-70°$ C. in 4-5 aliquots. The recrudescent variant was collected by cardiac puncture at the time of the second parasitaemia peak (28-32 days post-infection), and was stored similarly. These frozen aliquots were passaged once before experimental mice were infected.
Low Dose Infection Protocol Mice were given three i.v. infections at 3-4 week intervals with $10^5$ P.c.chabaudi AS primary variant PRBC. 48 hours after each infection mice were administered Malarone, as described above, to eliminate all live parasites and achieve a low parasite dose. Naïve control mice were injected with PBS and administered Malarone at the same time points. In separate experiments, around 40 days after the third infection mice were challenged with $10^6$ P.c.chabaudi AS primary variant PRBC (homologous parasite) or either $10^6$ P.c.chabaudi AS recrudescent variant PRBC or $10^6$ P.c.chabaudi CB PRBC (heterologous parasites) and the parasitaemia monitored by blood smears every 2 days.
Cell Culture Medium Cells were cultured in Minimum Essential Medium Eagle (EMEM) (Trace Scientific Ltd, Melbourne, Vic, Aust.) supplemented with 5% or 10% heat inactivated foetal calf serum (FCS) (JRH Bioscience, Lexena, Kans., USA), 50 µg/ml streptomycin (CSL Ltd., Parkville, Vic, Aust), 100 µg/ml penicillin (CSL Ltd.) and 55 µM 2-mercaptoethanol (GibcoBRL, Grand Island, N.Y., USA)—complete culture medium (CCM).
Collection of PRBC and Normal Mouse RBC for Proliferation Assays Blood was collected by cardiac puncture into heparinised Vacutainers from naïve mice and from infected mice with parasitaemias between 20-40%. Blood was washed twice in sterile PBS, then PRBC were resuspended at $1\times10^8$ pRBC/ml in culture medium+10% FCS. Normal mouse RBC (nmRBC) were diluted to an equivalent concentration. Cells were aliquoted and stored at $-20°$ C. until required.
Isolation of Mononuclear Cells from Spleens Spleens from low dose and control naïve mice were harvested under aseptic conditions just prior to the challenge infection and single cell suspensions were prepared. RBC were lysed using Gey's Erythrocyte Lysis Buffer [MacPherson G. G., 1998 #315] and mononuclear cells isolated by density centrifugation over NycoPrep 1.077 (Axis-Shield PoC AS, Oslo, Norway).
Proliferation Assays of Splenic Mononuclear Cells Proliferation assays were performed in 96-well flat bottom tissue culture plates (Corning Incorporated, Corning, N.Y., USA). Single cell suspensions were diluted to $2\times10^6$ cells/ml in 5% FCS/CCM. Cells were stimulated in triplicate with P.c.chabaudi AS-PRBC or P.c.chabaudi CB-PRBC at final concentrations of $1\times10^7$, $5\times10^6$ or $2.5\times10^6$ PRBC/ml, nmRBC at an equivalent concentration of RBC/ml or Concanavalin A (Con A) at 10 µg/ml. Cells were incubated for 3 days, then pulsed with 0.25 µCi/well of $^3$H-thymidine (NEN, Boston, Mass., USA) for a further 18-24 hr. Cells were harvested onto fibreglass filter mats using a cell harvester (Harvester 96, Tomtec, Hamden, CT, USA), and radioactivity was measured in a Wallac 1205 Betaplate liquid scintillation counter.
Annexin-V-fluos Staining of Splenic Mononuclear Cells MAbs were diluted at 1/50 and used at 50 ul per $5\times10^5$ cells. Incubations were performed on ice in the dark for 30 min. Spleen cells were single-stained with CD4-PE, CD8-PE or CD19-PE. After 2 washes in FACS Buffer (1% FCS and 0.01% w/v sodium azide in PBS), cells were stained for 15 min with the Annexin-V-Fluos Staining Kit (Roche Diagnostics) according to the manufacturer's instructions and washed once in FACS Buffer. Fluorescence was measured using a FACSCalibur (BD) and data were analysed using CellQuest software (BD).
Staining of Parasite Antigens on the Surface of PRBC This procedure was based on previously described methods Gilks et al, 1990, Parasite Immunol 12 45; Staalsoe et al, 1999, Cytometry 35 329. Mice used as a source of PRBC were kept in a reverse light-cycle (2000 hrs-0800 hrs) so that late stage parasites could be collected in the morning. These mice were infected from frozen aliquots of P.c.chabaudi AS or *P.c.chabaudi* CB. When parasitaemia reached 10-20%, mice were sacrificed at around 1030 hrs and blood was collected by cardiac puncture into heparinised Vacutainers (Becton Dickinson). After two washes in RPMI/HEPES, cells were resuspended at 5% haematocrit in RMPI/HEPES/ NaHCO$_3$/10% FCS and cultured for 3-4 hours in 5% CO$_2$, 5% O$_2$ at 37° C. until late stage parasites were evident. Cells were then washed 3 times in PBS/1% FCS and resuspended at 0.2% haematocrit. 100 ul of cells were then stained using a 3-step method, sequentially incubated with a 1/10 dilution of mouse serum, goat anti-mouse IgG (1/50 dilution, Caltag) and FITC-conjugated swine anti-goat IgG (1/20 dilution, Caltag) plus ethidium bromide (20ug/ml). All incubations were for 30 mins at room temperature and cells were washed twice in PBS/1% FCS between each step. Fluorescence was measured on a FACSCalibur. Late stage parasites were gated based on higher forward scatter and side scatter properties than other RBC and 1000 events were counted per test. Data were analysed using CellQuest software.

Hyperimmune Serum

Mice were given 3 i.v. infections at 3-4 week intervals with 10$^5$ *P.c.chabaudi* AS PRBC and the infection allowed to self-cure. These mice were exposed to high doses of PRBC and had near complete protection upon rechallenge with homologous parasites. Blood containing high titres of specific antibodies was obtained from these mice by tail bleed 3 weeks after the third infection.

EXAMPLE 9

A Single Low Dose Infection Primed Antigen-specific Splenic Lymphocytes without Inducing Lymphocyte Apoptosis Previous data has shown that infection with *Plasmodium* results in elevated levels of apoptosis in T and B lymphocytes Balde et al, 1995, Immunol Lett 46 59; Helmby et al, 2000, Infect Immun 68 1485, and that *Plasmodium* specific T cells are deleted following *Plasmodium* infection (Hirunpetcharat et al, 1998, Proc Natl Acad Sci USA 95 1715). The present investigators proposed that administration of a low dose of live parasite (infection followed by drug cure 48 hours later) would be sufficient to prime lymphocytes, but avoid the apoptotic deletion associated with an unlimited infection.

To investigate this, mice were administered a single infection with 1×10$^5$ *P.c.chabaudi* AS PRBC. On day 2 post-infection, a sub-set of infected mice and naïve controls (injected with PBS at the time of infection) were sacrificed and splenic lymphocyte subsets (CD4, CD8 and CD19) were examined for evidence of apoptosis using Annexin V. Antigen-specific proliferative responses of splenic lymphocytes were also examined. After 2 days, infected mice showed no higher levels of Annexin V staining on any of the lymphocyte subsets examined, compared with naive mice (FIG. 6). Lympho-proliferative responses to crude parasite antigen were minimal and similar in naïve and infected mice.

From day 2, one group of the remaining mice were drug-cured (low dose) while the infection was allowed to continue in another group (high dose). When the high dose group reached peak parasitaemia on day 8, both groups, along with a group of naive control mice, were sacrificed and Annexin V staining and antigen-specific lympho-proliferative responses were assessed. A significantly higher percentage of CD4 and CD8 positive splenic lymphocytes from mice that had a high dose were positive by Annexin V staining compared with naive mice (P<0.05). In contrast, low dose mice had no more apoptotic cells than naive controls. In lympho-proliferation assays, cells from high dose mice showed no greater response to parasite antigen than cells from naive control mice, and the response to ConA was significantly lower (P<0.05). In contrast, splenic lymphocytes from low dose mice showed significantly higher levels of proliferation in response to all doses of parasite antigen, compared with lymphocytes from naive mice (P<0.05).

EXAMPLE 10

Low Dose Infection Induced Significant Protection Against a Homologous Parasite Challenge and Against Challenge with a Different Parasite Strain or Variant Once it was established that a low dose infection could prime lymphocytes without inducing apoptosis, protection induced by multiple low dose infections was examined. Mice exposed to 3 cycles of infection with *P.c.chabaudi* AS were significantly protected on re-challenge with homologous parasites compared with naïve mice (P<0.001) (FIG. 7-A/B). Whereas naïve mice had high peak parasitaemias (mean+/−SEM: 37.7% +/−1.1) followed by multiple recrudescent peaks, low dose mice rapidly controlled the primary peak (mean+/−SEM: 1.5% +/−0.5) and rarely developed recrudescence.

To examine the specificity of immunity induced by low dose infection, mice exposed to 3 low dose infections with *P.c.chabaudi* AS together with naïve controls were challenged with homologous parasites, or with a different parasite strain or variant. Mice given low dose infection showed significantly reduced peak parasitaemias during challenge with the heterologous strain *P.c.chabaudi* CB (P<0.01) compared with naïve mice (FIG. 7A). In low dose mice there was no significant difference in peak parasitaemia during homologous compared with heterologous challenge (P=0.51), suggesting immunity induced by low dose infection was predominantly targeting determinants that were commonly expressed between the two strains.

Previous studies have shown that parasite variants expressed during recrudescence differ from those expressed during the primary peak {McLean, 1982 #85}. In a separate experiment, mice exposed to low dose infection with *P.c.chabaudi* AS primary variant parasites (collected from a donor mouse during primary peak) and naïve controls, were challenged with homologous parasites or with *P.c.chabaudi* AS recrudescent variant is parasites (collected during recrudescence in the same donor mouse) (FIG. 7B). Mice exposed to low dose infection with *P.c.chabaudi* AS primary variant parasites had significantly lower peak parasitaemias during challenge with homologous parasites or with parasites differing only in expression of the variant protein, compared with naïve mice (P<0.001).

EXAMPLE 11

Splenic Lymphocytes from Low Dose Mice Showed Significant Antigen-specific Proliferation in vitro Spleen cells collected prior to challenge infection from mice given 3 low dose infections with *P.c.chabaudi* AS proliferated strongly in response to in vitro stimulation with crude AS or CB parasite antigen (P<0.01 compared with naïve mice) (FIG. 8). This suggested that T cells specific for antigens commonly expressed on both strains were being primed.

EXAMPLE 12

Low Dose Infection Induced High Levels of Parasite Specific IgG but Failed to Generate IgG to Variant Antigens on the Surface of PRBC Prechallenge sera from mice exposed to low dose infections with *P.c.chabaudi* AS and hyper-immune serum obtained from mice allowed to self-cure following multiple infections with *P.c.chabaudi* AS had equivalent high titre IgG by ELISA and immunofluorescence. In contrast, hyper-immune sera had significantly higher levels of IgG (as measured by flow cytometry) that recognised the surface of homologous *P.c.chabaudi* AS PRBC (P<0.01) compared to low dose sera (FIG. 9). Low dose sera bound both *P.c.chabaudi* AS and *P.c.chabaudi* CB PRBC to a similar degree with the level of binding only just over that of naïve sera. Hyper-immune sera also showed only low level binding to *P.c.chabaudi* CB PRBC. Although commonly expressed merozoite and intracellular antigens appear to be targets of antibody responses induced by both high dose and low dose infection only high dose infections appear to induce antibodies against antigens expressed on the surface of PRBC. This supports the data shown in humans that a natural infection induces antibodies targeting variant surface antigens and indicates that the immunity induced by a low dose infection differs from that of a high dose infection.

EXAMPLE 13

Low Dose, Killed Parasite, Combined with CpG and Alum Induces Significant Protection Against Challenge and Prevents Recrudescence.

In a preferred form of the invention, a pharmaceutical composition comprises a low dose of non-living (i.e. killed) antigenic component from a pathogen, such as *Plasmodium* spp, and an agent capable of inducing endogenous IL-12, such as a CpG nucleic acid. The pharmaceutical composition may further comprise alum. Such a preferred pharmaceutical composition may be prepared using the methods described for example in Example 1 and below. The pharmaceutical composition may be administered to a mammal, such as a human or mouse, as described herein. Preferably, the low dose of the non-living antigenic component is equivalent to about 1,000 to 3,000 live parasites per milliliter of blood in the animal, prepared as described herein. A low dose may also be selected from a value less than $1\times10^7$, $1\times10^6$, $1\times10^5$, $1\times10^4$, $1\times10^3$, $1\times10^2$ or even less than 10 equivalent whole killed *Plasmodium* per milliliter of blood in the animal, or per mouse as described hereinafter.

Studies described in previous examples demonstrate that various combinations of low dose, live parasite combined with alum and CpG protect against parasite infection. This EXAMPLE shows for the first time that a low dose of killed parasite, combined with CpG and alum, in animals significantly protects against parasite infection, resolves parasite infection earlier, and prevents re-emergence of the disease (recrudescence).

Methods

Preparation of Dead *Plasmodium chabaudi chabaudi* AS Parasite Antigen

*Plasmodum Chabaudi chabaudi* AS was passaged through naive C57BL/6 and A/J mice. At peak parasitemia, mice were sacrificed by $CO_2$ inhalation and bled by cardiac puncture. Heparinised blood comprising parasites was centrifuged at 300×g for 10 mins. Supernatant was discarded and a pellet comprising parasites was subjected to two rounds of lysis in distilled water, followed by centrifugation for 25 minutes at ×10,000 rpm at 4° C. The pellet (comprising parasite components) was resuspended in PBS (0.5 mls) and then subjected to multiple (three) cycles of freezing (−70° C.) and thawing (37° C.). Crude parasite antigen was then passaged through a 26 gauge needle, and then suspended in PBS to an equivalent of $2.5\times10^8$ pRBC/ml. Aliquots of 1 ml were stored at −70° C. for immunization studies.

CpG Preparation

CpG-ODN 1826 (stimulatory motif) and Control CpG-ODN 1982 (control CpG, no stimulatory sequence) was purchased from Sigma Genosys Australia and stored at 10 mg/ml in PBS.

Alum

Commercially prepared alum (imject™; Pierce/Endogen) was absorbed 1:1 with killed parasite or in PBS (parasite vehicle) prior to immunizing mice.

| Immunization Schedule | |
|---|---|
| Protection study | |
| Day 0 | Primary immunization of A/J mice with CpG (100 μg/mouse), alum (50 μl), combined CpG plus alum, or combined CpG alum plus killed $1 \times 10^3$, $1 \times 10^5$, or $1 \times 10^7$ *P.c.chabaudi* parasites. |
| Day 21 | Animals boosted with killed $1 \times 10^3$, $1 \times 10^5$, or $1 \times 10^7$ *P.c.chabaudi* parasites (ip) diluted in PBS or PBS alone. |
| Day 42 | Animals boosted with killed $1 \times 10^3$, $1 \times 10^5$, or $1 \times 10^7$ *P.c.chabaudi* parasites (ip) or PBS alone. |
| Day 56 | Challenge mice with $1 \times 10^5$ *p Chabaudi* (iv). |
| Recrudescence Study | |
| Day 0 | Primary immunization of C57BL/6 mice with CpG (100 μg/mouse), alum (50 μl), combined CpG plus alum, or combined CpG, alum plus killed $1 \times 10^3$, $1 \times 10^5$, or $1 \times 10^7$ *P.c.chabaudi* parasites. |
| Day 21 | Animals immunised with killed $1 \times 10^3$, $1 \times 10^5$, or $1 \times 10^7$ *P.c.chabaudi* parasites (ip) or PBS (vehicle). |
| Day 42 | Challenge mice with $1 \times 10^5$ *p Chabaudi* (iv). |

Parasitaemia

Parasitaemia was determined from tail bleed smears every 2 days.

Results and Discussion

Protection Study. Peak parasitemia occurred in all control groups (Group A-C) at 10 days post infection (FIG. 10). The highest level of parasitaemia was observed in Control Group C, that had been primed with CpG plus alum (9.37±10.58). In all groups that had been immunized with killed parasite, parasitaemia was siginificantly reduced (D: $1\times10^7$, 0.03±0.03 (n=5); E: $1\times10^5$, 0.04±0.04 (n=4); F: $1\times10^3$ 0.01±0.01 (n=2)). Of significance, only 2 out of 5 (40%) animals immunized with dead, low dose parasite had detectable parasitemia during the 30 day course of the experiment. That is, 60% of animals were completely protected from infection. In addition, these two animals had a delayed on set of detectable parasitemia (Day 12). These data clearly show that immunization with low dose of killed parasite, combined with CpG and alum induces significant protection against parasite challenge.

Recrudescence Study

Recrudescence is the process by which parasites switch their expression of different variant surface antigens in order to evade the immune response, and then re-multiply. The new parasite clone, therefore is no longer recognized by the immune system and it may have a slightly different phenotype in terms of tissue adhesion, that may result in different pathology. Eventually the host immune systems adapts and recognizes the parasite, to only have the process of recrudescence continue, resulting in sequential peaks of parasite density in the blood. Antibodies to the merozoite surface appear to constitute one important factor in controlling recrudescence, while cell mediated immunity may be another factor. Therefore, in animals and humans where it is thought that the parasite infection has been resolved, re-emergence of parasitemia occurs. This next study aimed to investigate whether low dose immunization could also prevent recrudescence as well as reduce parasitemia.

In this study, peak parasitaemia was again reduced in all groups that had been immunized with killed parasite (data not shown). Animals that had been immunized with the low dose, dead parasite had completely resolved the infection by day 12, as compared to day 20 in control groups (Control CpG+ alum, alum alone, CpG alone, combined CpG plus alum). Animals immunized with higher doses of parasite, also completely resolved infection before controls ($1\times10^7$ at Day 14, and $1\times10^5$ at Day 16).

Data in FIG. 11 show that animals immunized with low doses of parasite ($1\times10^3$ and $1\times10^5$) also significantly inhibited recrudescence.

These data clearly show that immunization with low doses of parasite, can protect animals against parasitaemia, resolve infection earlier, and prevent re-emergence of the disease (recrudescence).

It is understood that the invention described in detail herein is susceptible to modification and variation, such that embodiments other than those described herein are contemplated which nevertheless fall within the broad scope of the invention.

The disclosure of each patent and scientific document, computer program and algorithm referred to in this specification is incorporated by reference in its entirety.

REFERENCES

1. Alfonso, L. C. C., T. M. Scharton, L. Q. Vieira, M. Wysocka, G. Trinchieri, and P. Scott. 1994. The adjuvant effect of interleukin-12 in a vaccine against *Leishmania major*. Science 263:235-237.
2. Amante, F. H., and M. F. Good. 1997. Prolonged Th1-like response generated by a *Plasmodium yoelii*-specific T cell clone allows complete clearance of infection in reconstituted mice. Parasite Immunol. 19:111-126.
3. Artavanis-Tsakonas, K., and E. M. Riley. 2002. Innate immune response to malaria: rapid induction of IFN-☐ from human NK cells by live *Plasmodium falciparum*-infected erythrocytes. J. Immunol. 169:2956-2963.
4. Braziolot-Millan, C. L., R. Weeratna, A. M. Krieg, C. A. Siegrist, and H. L. Davis. 1998. CpG DNA can induce strong Th1 humoral and cell-mediated immune responses against hepatitis B surface antigen in young mice. Proc. Natl. Acad. Sci. USA 95:1555-1558.
5. Davis, H. L., R. Weeratna, T. J. Waldschmidt, L. Tygrett, J. Schorr, and A. M. Krieg. 1998. CpG is a potent enhancer of specific immunity in mice immunized with recombinant hepatitis B surface antigen. J. Immunol. 160:870-876.
6. Deloran, P., C. Chougnet, J.-P. Lepers, S. Tallet, and P. Coulanges. 1991. Protective value of elevated levels of ☐ interferon in serum against exoerythrocytic stages of *P. falciparum*. J. Clin. Microbiol. 29:1757-1760.
7. Demi, L., R. Schirmbeck, J. Reimann, H. Wolf, and R. Wagner. 1999. Immunostimulatory CpG motifs trigger a T helper-1 immune response to human immunodeficiency virus type-1 (HIV) gp160 envelop proteins. Clin. Chem. Lab. Med. 37:199-204.
8. Dodoo, D. F. Omer, J. Todd, B. Akanmori, K. Koram, and E. Riley. 2002. Absolute levels and ratios of pro-inflammatory and anti-inflammatory cytokine production in vitro predict clinical immunity to *P. falciparum* malaria. J. Infect. Dis. 185:971-979.
9. DeSouza, J. B., K. H. Williamson, T. Otani, and J. H. Playfair. 1997. Early gamma interferon responses in lethal and nonlethal murine blood-stage malaria. Infect. Immun. 65:1593-1598.
10. Facer, C. A., and M. Tanner. 1997. Clinical trials of malaria vaccines: progress and prospects. Adv. Parasitol 39:1-68.
11. Favre, N., B. Ryffel, G. Bordmann, and W. Rudin. 1997. The course of *Plasmodium chabaudi chabaudi* infections in interferon-gamma receptor deficient mice. Parasite Immunol. 19:375-383.
12. Gately, M. K., L. M. Renzetti, J. Magram, A. S. Stern, L. Adorini, U. Gubler, and D. H. Presky. 1998. The interleukin-12/interleukin-12 receptor system: role in normal and pathogenic immune responses. Annu. Rev. Immmunol. 16:495-521.

TABLE 1

| | Proliferation | Cytokine Levels | | | |
|---|---|---|---|---|---|
| Group[a] | Antigen (cpm ± SEM) | IFN-γ ng/ml | TNF-α pg/ml | IL-4 pg/ml | IL-10 pg/ml |
| Untreated | 526 ± 71 | 0.39 ± 0.39 | 98.41 ± 10.22 | 254.27 ± 52.80 | 0.76 ± 0.01 |
| Antigen | 486 ± 44 | 5.13 ± 0.36 | 122.03 ± 17.78 | 178.55 ± 45.13 | 1.07 ± 0.11 |
| Antigen + Alum | 1162 ± 128 | 3.83 ± 0.86 | 175.03 ± 20.93 | 234.52 ± 20.60 | 1.27 ± 0.10 |
| Antigen + IL-12 | 768 ± 130 | 11.14 ± 2.27 | 189.85 ± 28.58 | 134.19 ± 33.22 | 1.01 ± 0.09 |
| Antigen + IL-12 + Alum | 2768 ± 622[b] | 43.13 ± 5.20[c] | 341.94 ± 44.26[c] | 165.87 ± 42.82[d] | 1.44 ± 0.14[e] |

[a]Groups of A/J mice (5 per group) were immunized s.c. with malaria antigen alone, antigen in alum, antigen plus 1.0 μg IL-12, or antigen plus 1.0 μg IL-12 in alum and boosted 3 weeks later by i.p. injection with antigen. Data from one of two replicate experiments are presented.
[b]$p < 0.05$ for Antigen + Alum vs Antigen + IL-12 + Alum
[c]$p < 0.0001$ for Antigen + Alum vs Antigen + IL-12 + Alum
[d]$p < 0.01$ for Antigen + Alum vs Antigen + IL-12 + Alum
[e]$p < 0.008$ for Antigen + Alum vs Antigen + IL-12 + Alum

TABLE 2

| Group[a] | Peak Parasitemia (%) Mean ± SEM | Clearance by Day | Survival % |
|---|---|---|---|
| Untreated (n = 10) | 41.25 ± 1.29 | — | 0 |
| 2 weeks post boost (n = 5) | 15.80 ± 2.29[b] | 14 | 100 |
| 12 weeks post boost (n = 5) | 28.65 ± 1.29[c] | 15 | 100 |

[a]Groups of A/J mice (n = 5) were immunized s.c. with antigen plus 1.0 μg IL-12 admixed in alum and boosted 3 weeks later by i.p. injection with antigen. For each immunization group, age-matched, untreated and immunized mice were infected i.p. with $10^6$ PRBC at 2 or 12 weeks post boost. Since there were no significance differences in peak parasitemia or survival between the two untreated groups (n = 10), data have been pooled.
[b]$p < 0.001$ compared to control
[c]$p < 0.001$ compared to control 13. Good, M. F. 2001. Towards a blood-stage vaccine for malaria: are we following all the leads? Nature Rev. Immunol. 1:117-125.
14. Good, M. F. and D. L. Doolan. 1999. Immune effector mechanisms in malaria. Curr. Opin. Immunol. 11:412-419.
15. Gramzinski, R. A., D. L. Doolan, M. Sedegah, H. L. Davis, S. M. Krieg, and S. L. Hoffman. 2001. Interleukin-12- and gamma interferon-dependent protection against malaria conferred by CpG oligodeoxynucleotide in mice. Infect. Immun. 69:1643-1649.
16. Heinzel, F. P., R. M. Rerko, F. Ahmed, and A. M. Hujer. 1996. IFN-☐ independent production of IL-12 during murine endotoxemia. J. Immunol. 157:4521-4528.
17. Holder, A. A. 1999. Malaria vaccines. Proc. Natl. Acad. Sci. USA 96:1167-1169.
18. James, S., and L. Miller. 2000. Malaria vaccine development: status report. Nature Med. Special Focus: Malaria, p. 9-13.
19. Jankovic, D., P. Caspar, M. Zweig, M. Garcia-Moll, S. D. Showalter, F. R. Vogel, and A. Sher. 1997. Adsorption to aluminum hydroxide promotes the activity of IL-12 as an adjuvant for antibody as well as type 1 cytokine responses to HIV-1 gp120. J. Immunol. 159:2409-2417.
20. Jankovic, D., T. A. Wynn, M. C. Kullberg, S. Hieny, P. Caspar, S. James, A. W. Cheever, and A. Sher. 1999. Optimal vaccination against *Schistosoma mansoni* requires the induction of both B cell- and IFN-☐-dependent effector mechanisms. J. Immunol. 162:345-351.
21. Kenney, R. T., D. L. Sacks, J. P. Sypek, L. Vilela, A. A., Gam, and K. Evans-Davis. 1999. Protective immunity using recombinant human IL-12 and alum as adjuvants in a primate model of cutaneous leishmaniasis. J. Immunol. 163: 4481-4488.
22. Kitamura, D., J. Roes, R. Kuhn, and K. Rajewsky. 1991. A B cell-deficient mouse by targeted disruption of the membrane exon on the immunoglobulin mu chain gene. Nature 350:423-426.
23. Klinman, D., A.-K. Yi, S. L. Beaucage, J. Conover, and A. M. Krieg. 1996. CpG motifs present in bacterial DNA rapidly induce lymphocytes to secrete IL-6, IL-12 and IFN-☐. Proc. Natl. Acad. Sci. USA 93:2879-2883.
24. Langhorne, J., S. J. Quin, and L. A. Sanni. 2002. Mouse models of blood-stage malaria infections: immune responses and cytokines involved in protection and pathology, p. 204-228. In P. Perlmann and M. Troye-Blomberg (ed.), Malaria immunology. Karger, Basel.
25. Langhorne, J., B. Simon-Haarhaus, and S. J. Meding. 1990. The role of CD4$^+$ T cells in the protective immune response to *Plasmodium chabaudi* in vivo. Immunol. Letters. 25:101-108.
26. Luty, A. J. F., B. Lell, R. Schmidt-Ott, L. G. Lehman, D. Luckner, B. Greve, P. Matousek, K. Herbich, D. Schmidt, F. Migot-Nabias, P. Deloran, R. S. Nussenzweig, and P. G. Kremsner. 1999. Interferon-☐ responses are associated with resistance to reinfection with *Plasmodium falciparum* in young African children. J. Infect. Dis. 179:980-988.
27. Miller, M. A., M. J. Skeen, and H. K. Ziegler. 1997. A synthetic peptide administered with IL-12 elicits immunity to *Listeria monocytogenes*. J. Immunol. 159:3675-3679.
28. Mohan, K., P. Moulin, and M. M. Stevenson. 1997. NK cell cytokine production not cytotoxicity contributes to resistance against blood-stage *Plasmodium chabaudi* AS infection. J. Immunol. 159:4990-5004.
29. Mohan, K., and M. M. Stevenson. 1998. Acquired immunity to asexual blood stages, p. 467-493. In I. W. Sherman (ed), Malaria: parasite biology, pathogenesis, and protection, American Society Microbiology, Washington, D.C.
30. Near, K. A., A. W. Stowers, D. Jankovic, and D. C. Kaslow. 2002.
Improved immunogenecity and efficacy of the recombinant 19-kilodalton merozoite surface protein 1 by addition of oligodeoxynucleotide and aluminum hydroxide gel in a murine malaria vaccine model. Infect. Immun. 70:692-701.
31. O'Garra, A., and K. Murphy. 1994. Role of cytokines in determining T-lymphocyte function. Curr. Opin. Immunol. 6:458-466.
32. Plebanski, M. and A. Hill. 2000. The immunology of malaria infection. Curr. Opin. Immunol. 12:437-441.
33. Podoba, J. E., and M. M. Stevenson. 1991. CD4$^+$ and CD8$^+$ T lymphocytes both contribute to acquired immunity to blood-stage *Plasmodium chabaudi* AS. Infect. Immun. 59:51-58.
34. Sam, H., and M. M. Stevenson. 1999. In vivo IL-12 production and IL-12 receptors ☐1 and ☐2 mRNA expression in the spleen are differentially upregulated in resistant B6 and susceptible A/J mice during early blood-stage *Plasmodium chabaudi* AS malaria. J. Immunol. 162:1582-1589.
35. Stacey, K. J., and J. M. Blackwell. 1999. Immunostimulatory DNA as an adjuvant in vaccination against *Leishmania major*. Infect. Immun. 67:3719-3726.
36. Stevenson, M. M., J. J. Lyanga, and E. Skamene. 1982. Murine malaria: genetic control of resistance to *Plasmodium chabaudi*. Infect. Immun. 38:80-88.
37. Stevenson, M. M., M. F. Tam, S. F. Wolf, and A. Sher. 1995. IL-12 induced protection against blood-stage *Plasmodium chabaudi* AS requires IFN-☐ and TNF-☐ and occurs via an NO-dependent mechanism. J. Immunol. 155: 2545-2556.
38. Stevenson, M. M. and M. F. Tam. 1993. Differential induction of helper T cell subsets during blood-stage *Plasmodium chabaudi* AS infection in resistant and susceptible mice. Clin. Exp. Immunol. 92:77-83.
39. Su, Z., and M. M. Stevenson. 2002. IL-12 is required for antibody-mediated protective immunity against blood-stage *Plasmodium chabaudi* AS malaria infection in mice. J. Immunol. 168:1348-1355.
40. Su, Z., and M. M. Stevenson. 2000. Central role of endogenous gamma interferon in protective immunity against blood-stage *Plasmodium chabaudi* AS infection. Infect. Immun. 68:4399-4406.
41. Taylor-Robinson, A. W., and R. S. Philips. 1994. B cells are required for the switch from TH1- to TH2-regulated immune response to *Plasmodium chabaudi chabaudi* infection. Infect. Immun. 62:2490-2498.
42. van der Heyde, H. C., B. Pepper, J. Batchelder, F. Cigel, and W. P. Weidanz. 1997. The time course of selected malarial infections in cytokine-deficient mice. Exp. Parasitol. 88:206-213.
43. von der Weid, T. and J. Langhorne. 1993. Altered response of CD4$^+$ T cell subsets to *Plasmodium chabaudi chabaudi* in B cell-deficient mice. Int. Immunol. 5:1343-1348.
44. von der Weid, T. N. Honarvar, and J. Langhorne. 1996. Gene-targeted mice lacking B cells are unable to eliminate a blood stage malaria infection. J. Immunol. 156:2510-2516.
45. Weeratna, R. D., M. J. McCluskie, Y. Xu, and H. S. Davis. 2000. CpG DNA induces stronger immune responses with less toxicity than other adjuvants. Vaccine 18:1755-1762.
46. Wynn, T. A., A. W. Cheever, D. Jankovic, R. W. Poindexter, P. Caspar, F. A. Lewis, and A. Sher. 1995. An IL-12-based vaccination method for preventing fibrosis induced by schistosome infection. Nature 376:594-596.

47. Wynn, T. A., D. Jankovic, S. Hieny, A. W. Cheever, and A. Sher. 1995. IL-12 enhances vaccine-induced immunity to *Schistosoma mansoni* in mice and decreases T helper 2 cytokine expression, IgE production, and tissue eosinophilia. J. Immunol. 154:4701-4709.
48. Wynn, T. A., A. Reynolds, S. James, A. W. Cheever, P. Caspar, S. Hieny, D. Jankovic, M. Strand, and A. Sher. 1996. IL-12 enhances vaccine-induced immunity to schistosomes by augmenting both humoral and cell-mediated immune responses against the parasite. J. Immunol. 157:4068-4078.
49. Yap, G. S., and M. M. Stevenson. 1994. Differential requirements for an intact spleen in induction and expression of B-cell-dependent immunity to *Plasmodium chabaudi* AS. Infect. Immun. 62:4219-4225.
50. Hoffman S L, et al. Science. 237:639, 1987.
51. Urban B C, et al. Nature. 400:73, 1999.
52. Xu H, et al. J Exp Med. 195:881, 2002.
53. Pombo, D J, et al. The Lancet 360:610, 2002.
54. Makobongo, M O, et al. PNAS 100:2628, 2003.
55. Gilks C F, et al. Parasite Immunol. 12:45, 1990.
56. Staalsoe T, et al. Cytometry. 35:329, 1999.
57. Balde A T, et al. Immunol Lett. 46:59, 1995.
58. Helmby H, et al. Infect Immun. 68:1485, 2000.
59. Hirunpetcharat C, et al. PNAS 95:1715, 1998.

The invention claimed is:

1. An immunogenic agent comprising:
   an antigenic component of less than $10^5$ killed whole parasites of at least one *Plasmodium* spp selected from the group consisting of *Plasmodium falciparum*, *Plasmodium vivax*, *Plasmodium malariae*, and *Plasmodium ovale*; and
   an agent capable of increasing an amount of IL-12 in a human,
   wherein the immunogenic agent is capable of eliciting an immune response to the *Plasmodium* spp in a human.

2. The immunogenic agent of claim 1 wherein the antigenic component comprises less than $10^3$ killed whole *Plasmodium* spp parasites.

3. The immunogenic agent of claim 1 wherein the *Plasmodium* spp is *Plasmodium falciparum*.

4. The immunogenic agent of claim 1 wherein the agent capable of increasing an amount of IL-12 in the human is capable of stimulating endogenous IL-12 expression in the human.

5. The immunogenic agent of claim 4 wherein the agent capable of increasing an amount of IL-12 in the human comprises a CpG nucleic acid.

6. The immunogenic agent of claim 5 wherein the CpG nucleic acid comprises a nucleotide sequence selected from the group consisting of:

```
TCGTCGTTTTGTCGTTTTGTC,      (SEQ ID NO: 1)

TCCATGACGTTCCTGACGTT         (SEQ ID NO: 2)
and

TCCAGGACTTCTCTCAGGTT.        (SEQ ID NO: 3)
```

7. The immunogenic agent of claim 1 wherein the agent capable of increasing an amount of IL-12 in the human is IL-12 protein.

8. The immunogenic agent of claim 7 wherein the IL-12 protein is human IL-12.

9. The immunogenic agent of claim 8 wherein the IL-12 protein is recombinant IL-12 protein.

10. The immunogenic agent of claim 8 wherein the IL-12 protein is isolated wild type IL-12 protein.

11. The immunogenic agent of claim 1 wherein the agent capable of increasing an amount of IL-12 in the human is a nucleic acid comprising a nucleotide sequence encoding IL-12 protein.

12. The immunogenic agent of claim 11 wherein the nucleic acid is operably linked to a promoter capable of expressing the nucleic acid in the human.

13. The immunogenic agent of claim 1 further comprising an adjuvant.

14. The immunogenic agent of claim 13 wherein the adjuvant is selected from the group consisting of: aluminum hydroxide (alum), IL-12, CpG-ODN, SBAS2, SBAS4, QS21 and ISCOM.

15. The immunogenic agent of claim 14 wherein the adjuvant is aluminum hydroxide.

16. A pharmaceutical composition comprising the immunogenic agent of claim 1 and a pharmaceutically-acceptable carrier.

17. The pharmaceutical composition of claim 16 wherein said pharmaceutical composition is an immunotherapeutic composition.

18. The pharmaceutical composition of claim 17 wherein the immunotherapeutic composition is a vaccine.

19. The pharmaceutical composition of claim 16, which when administered to the human is capable of reducing severity of or improving recovery from infection by one or more different *Plasmodium* spp.

20. The pharmaceutical composition of claim 19 wherein the one or more different *Plasmodium* spp comprises one or more different respective strains thereof.

21. The pharmaceutical composition of claim 18 wherein said vaccine is capable of providing protective immunity in the human against one or more different *Plasmodium* spp.

22. The pharmaceutical composition of claim 21 wherein the one or more *Plasmodium* spp comprises one or more respective strains thereof.

23. A method for inducing an immune response in a human, including the step of administering the pharmaceutical composition of claim 16 to the human.

24. The method of claim 23 wherein the pharmaceutical composition is an immunotherapeutic composition capable of reducing severity of infection by or improving recovery from infection by *Plasmodium* spp in the human.

25. The method of claim 24 wherein the immunotherapeutic composition is a vaccine capable of providing protective immunity or treating the human against one or more *Plasmodium* spp.

26. The immunogenic agent of claim 1 wherein the *Plasmodium* spp is in a developmental form selected from the group consisting of sporozoites, merozoites, gametocytes, ookinetes, and combinations thereof.

27. The immunogenic agent of claim 26 wherein the developmental form is merozoites.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: artificial
<220> FEATURE:
<223> OTHER INFORMATION: synthetic

<400> SEQUENCE: 1
tcgtcgtttt gtcgttttgt c                                     21

<210> SEQ ID NO 2
<211> LENGTH: 20
<212> TYPE: DNA
<213> ORGANISM: artificial
<220> FEATURE:
<223> OTHER INFORMATION: synthetic

<400> SEQUENCE: 2
tccatgacgt tcctgacgtt                                       20

<210> SEQ ID NO 3
<211> LENGTH: 20
<212> TYPE: DNA
<213> ORGANISM: artificial
<220> FEATURE:
<223> OTHER INFORMATION: synthetic

<400> SEQUENCE: 3
tccaggactt ctctcaggtt                                       20

<210> SEQ ID NO 4
<211> LENGTH: 19
<212> TYPE: DNA
<213> ORGANISM: artificial
<220> FEATURE:
<223> OTHER INFORMATION: synthetic

<400> SEQUENCE: 4
tccatgacgt tcctgagtt                                        19
```